(12) United States Patent
Palmer et al.

(10) Patent No.: US 7,326,784 B2
(45) Date of Patent: Feb. 5, 2008

(54) INTERMEDIATES FOR THE PREPARATION OF TRICYCLIC DIHYDROPYRANO-IMIDAZO-PYRIDINES DERIVATIVES

(75) Inventors: Andreas Palmer, Constance (DE); Ulrike Nettekoven, Basel (CH)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/582,609

(22) PCT Filed: Dec. 17, 2004

(86) PCT No.: PCT/EP2004/053562

§ 371 (c)(1), (2), (4) Date: Jun. 12, 2006

(87) PCT Pub. No.: WO2005/058894

PCT Pub. Date: Jun. 30, 2005

(65) Prior Publication Data

US 2007/0117786 A1    May 24, 2007

(30) Foreign Application Priority Data

Dec. 19, 2003  (EP) ................... 03029361
Jul. 23, 2004  (EP) ................... 04103550

(51) Int. Cl.
C07D 413/00 (2006.01)
C07D 401/00 (2006.01)
C07D 471/02 (2006.01)
C07D 405/00 (2006.01)
C07D 498/12 (2006.01)
C07D 491/12 (2006.01)

(52) U.S. Cl. ............ 544/127; 544/333; 546/83; 546/121

(58) Field of Classification Search ............ None
See application file for complete search history.

(56) References Cited

U.S. PATENT DOCUMENTS 4,468,400 A * 8/1984 Gold et al. ............ 514/292

FOREIGN PATENT DOCUMENTS

| EP | 0 718 265 B1 | 6/1996 |
|---|---|---|
| WO | 95/27714 A1 | 10/1995 |
| WO | 98/42707 A1 | 10/1998 |
| WO | 98/54188 A1 | 12/1998 |
| WO | 00/17200 A1 | 3/2000 |
| WO | 00/26217 A1 | 5/2000 |
| WO | 00/63211 A1 | 10/2000 |
| WO | 01/72754 A1 | 10/2001 |
| WO | 01/72755 A1 | 10/2001 |
| WO | 01/72756 A1 | 10/2001 |
| WO | 01/72757 A1 | 10/2001 |
| WO | 02/34749 A1 | 5/2002 |
| WO | 03/014120 A1 | 2/2003 |
| WO | 03/014123 A1 | 2/2003 |
| WO | 03/016310 A1 | 2/2003 |
| WO | 03/068774 A1 | 8/2003 |
| WO | 03/091253 A1 | 11/2003 |
| WO | 2004/050585 A1 | 6/2004 |
| WO | 2005/058325 A1 | 6/2005 |
| WO | 2005/090358 A2 | 9/2005 |

OTHER PUBLICATIONS

Kaminski, J.J., et al., "Antiulcer Agents. 4. Conformational Considerations and the Antiulcer Activity of Substituted Imidazo [1,2-a]pyridines and Related Analogues", *J. Med. Chem.*, vol. 32, p. 1686-1700, (1989).

Noyori, R., et al., "Asymmetrische Katalyse mit hinsichtlich Struktur und Funktion gezielt entworfenen Molekülen: die chemo- und stereoselektive Hydrierung von Ketonen", *Angew. Chem.*, vol. 113, p. 40-75, (2001).

* cited by examiner

*Primary Examiner*—James O. Wilson
*Assistant Examiner*—Erich Leeser
(74) *Attorney, Agent, or Firm*—The Nath Law Group; Joshua B. Goldberg; Sheldon M. McGee

(57) ABSTRACT

The invention relates to compounds of the formula 1,

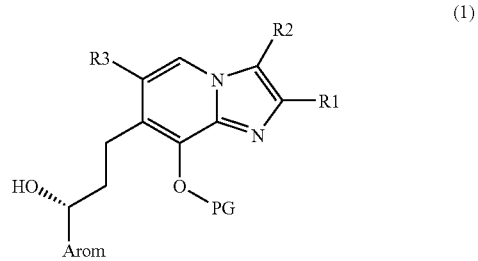

in which R1, R2, R3, Arom and PG have the meanings as indicated in the description. These compounds are valuable intermediates for the preparation of pharmaceutically active compounds.

12 Claims, No Drawings

INTERMEDIATES FOR THE PREPARATION OF TRICYCLIC DIHYDROPYRANO-IMIDAZO-PYRIDINES DERIVATIVES

This application is a 371 of application number PCT/EP04/53562, filed on Dec. 19, 2004, which claims foreign priority to EPO application numbers 03029361.7, filed on Dec. 19, 2003 and 04103550.2, filed on Jul. 23, 2004.

TECHNICAL FIELD

The invention relates to novel compounds, which are used in the pharmaceutical industry as valuable intermediates for the preparation of active compounds.

PRIOR ART

U.S. Pat. No. 4,468,400 describes tricyclic imidazo[1,2-]pyridines having different ring systems fused to the imidazopyridine skeleton, which compounds are said to be suitable for treating peptide ulcer disorders. The International Patent Applications WO 95/27714, WO 98142707, WO 98154188, WO 00/17200, WO 00/26217, WO 00163211, WO 01172756, WO 01/72754, WO 01/72755, WO 01/72757, WO 02/34749, WO 03/014120, WO 03/016310, WO 03/014123, WO 03/068774 and WO 03/091253 disclose tricyclic imidazopyridine derivatives having a very specific substitution pattern, which compounds are likewise said to be suitable for treating gastrointestinal disorders.

Kaminski et. al., J. Med. Chem. 1989, 32, 1686 describe the synthesis and configurations of imidazo[1,2-a]pyridines and their antiulcer activity.

DESCRIPTION OF THE INVENTION

It has now been found that the enantiomers of the compounds described for example in WO 03/014123 as racemic mixtures can be prepared stereoselectively by way of a reaction sequence which makes use of novel intermediates.

The invention thus relates in a first aspect to compounds of the formula 1,

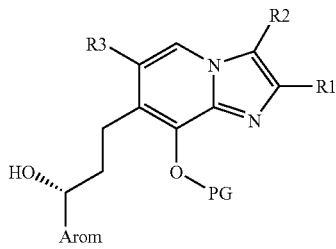
(1)

where
R1 is hydrogen, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl or hydroxy -1-4C-alkyl, R2 is hydrogen, 1-4C-alkyl, 3-7C-cycloalkyl, 3-7C-cycloalkyl-1-4C-alkyl, 1-4C-alkoxycarbonyl, hydroxy-1-4C-alkyl, hydroxy-3-4-C-alkenyl, hydroxy-3-4C-alkinyl, halogen, 2-4C-alkenyl, 2-4C-alkynyl, fluoro-1-4C-alkyl, cyanomethyl, 1-4C-alkoxy, 1-4C-alkylcarbonylamino, 1-4C-alkoxycarbonylamino, 1-4C-alkoxy-1-4C-alkoxycarbonylamino, 1-4C-alkylcarbonyl, 2-4C-alkenylcarbonyl, 2-4C-alkinylcarbonyl or the radical —CO—NR21R22, where
R21 is hydrogen, 1-7C-alkyl, hydroxy-1-4C-alkyl, 1-4C-alkoxy-1-4C-alkyl or 3-7C-cycloalkyl and
R22 is hydrogen, 1-7C-alkyl, hydroxy-1-4C-alkyl, 1-4C-alkoxy-1-4C-alkyl or 3-7C-cycloalkyl, or where
R21 and R22 together and including the nitrogen atom to which they are attached form a pyrrolidino, piperidino, morpholino, aziridino or azetidino radical, R3 is hydroxy-1-4C-alkyl, 1-4C-alkoxy-1-4C-alkyl, 1-4C-alkoxy-1-4C-alkoxy-1-4C-alkyl, 1-4C-alkoxycarbonyl, fluoro-1-4C-alkoxy-1-4C-alkyl, a imidazolyl, tetrazolyl or oxazolyl radical or the radical —CO—NR31 R32, where
R31 is hydrogen, 1-7C-alkyl, hydroxy-1-4C-alkyl, 1-4C-alkoxy-1-4C-alkyl or 3-7C-cycloalkyl and
R32 is hydrogen, 1-7C-alkyl, hydroxy-1-4C-alkyl, 1-4C-alkoxy-1-4C-alkyl or 3-7C-cycloalkyl, or where
R31 and R32 together and including the nitrogen atom to which they are attached form a pyrrolidino, piperidino, morpholino, aziridino or azetidino radical, Arom is a R4-, R5-, R6- and R7-substituted mono- or bicyclic aromatic radical selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where
R4 is hydrogen, 1-4C-alkyl, hydroxy-1-4C-alkyl, 1-4C-alkoxy, 2-4C-alkenyloxy, 1-4C-alkylcarbonyl, 1-4C-alkoxycarbonyl, carboxy-1-4C-alkyl, 1-4C-alkoxycarbonyl-1-4C-alkyl, halogen, aryl, aryl-1-4C-alkyl, aryloxy, aryl-1-4C-alkoxy, trifluoromethyl, nitro, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen or trifluoromethyl, R6 is hydrogen, 1-4C-alkyl or halogen and R7 is hydrogen, 1-4C-alkyl or halogen, PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4-C-alkyl substituted by a SIR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical SO₂—R11 wherein
R8, R9, R10 are independently from each other 1-7C-alkyl, aryl or aryl-1-4C alkyl, R11 is 1-4C-alkyl or aryl where
aryl is phenyl or substituted phenyl having one, two or three Identical or different substituents from the group consisting of 1-4-C-alkyl, 1-4C-alkoxy, carboxyl, 1-4C-alkoxycarbonyl, halogen, trifluoromethyl, nitro, trifluoromethoxy and cyano, and the salts of these compounds.

1-4C-Alkyl denotes straight-chain or branched alkyl radicals having 1 to 4 carbon atoms. Examples which may be mentioned are the butyl, isobutyl, sec-butyl, tertbutyl, propyl, isopropyl, ethyl and methyl radicals.

3-7C-Cycloalkyl denotes cyclopropyl, cyclobutyl, cyclopentyl, cyclohexyl and cycloheptyl, among which cyclopropyl, cyclobutyl and cyclopentyl are preferred.

3-7C-Cycloalkyl-1-4C-alkyl denotes one of the abovementioned 1-4C-alkyl radicals which is substituted by one of the abovementioned 3-7C-dialkyl radicals. Examples which may be mentioned are the cyclopropylmethyl, the cyclohexylmethyl and the cyclohexylethyl radicals.

1-4C-Alkoxy denotes radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

1-4C-Alkoxy-1-4C-alkyl denotes one of the abovementioned 1-4C-alkyl radicals which is substituted by one of the abovementioned 1-4C-alkoxy radicals. Examples which may be mentioned are the methoxymethyl, the methoxyethyl and the butoxyethyl radicals.

1-4C-Alkoxycarbonyl (—CO-1-4C-alkoxy) denotes a carbonyl group to which is attached one of the abovementioned 1-4C-alkoxy radicals. Examples which may be mentioned are the methoxycarbonyl ($CH_3O$—C(O)—) and the ethoxycarbonyl ($CH_3CH_2O$—C(O)—) radicals.

2-4C-Alkenyl denotes straight-chain or branched alkenyl radicals having 2 to 4 carbon atoms. Examples which may be mentioned are the 2-butenyl, 3-butenyl, 1-propenyl and the 2-propenyl (allyl) radicals.

2-4C-Alkynyl denotes straight-chain or branched alkynyl radicals having 2 to 4 carbon atoms. Examples which may be mentioned are the 2-butynyl, the 3-butynyl and, preferably, the 2-propynyl (propargyl radicals).

Fluoro-1-4C-alkyl denotes one of the abovementioned 1-4C-alkyl radicals which is substituted by one or more fluorine atoms. An example which may be mentioned is the trifluoromethyl radical.

Hydroxy-1-4C-alkyl denotes abovementioned 1-4C-alkyl radicals which are substituted by a hydroxyl group. Examples which may be mentioned are the hydroxymethyl, the 2-hydroxyethyl and the 3-hydroxypropyl radicals.

3-4C-Alkenyl denotes straight-chain or branched alkenyl radicals having 3 to 4 carbon atoms. Examples which may be mentioned are the 2-butenyl, 3-butenyl, 1-propenyl and the 2-propenyl (allyl) radicals.

3-4C-Alkynyl denotes straight-chain or branched alkynyl radicals having 3 to 4 carbon atoms. Examples which may be mentioned are the 2-butynyl, the 3-butynyl and, preferably, the 2-propynyl (propargyl) radicals.

Hydroxy-3-4-C-alkenyl denotes abovementioned 3-4C-alkenyl radicals which are substituted by a hydroxyl group. Examples which may be mentioned are the 1-hydroxypropenyl or the 1-hydroxy-2-butenyl radical.

Hydroxy-3-4-C-alkinyl denotes abovementioned 3-4-C-alkinyl radicals which are substituted by a hydroxyl group. Examples which may be mentioned are the 1-hydroxypropinyl or the 1-hydroxy-2-butinyl radical.

For the purpose of the invention, halogen is bromine, chlorine and fluorine.

1-4C-Alkoxy-1-4C-alkoxy denotes one of the abovementioned 1-4C-alkoxy radicals which is substituted by a further 1-4C-alkoxy radical. Examples which may be mentioned are the radicals 2-(methoxy)ethoxy ($CH_3$—O—$CH_2$—$CH_2$—O—) and 2-(ethoxy)ethoxy ($CH_3$—$CH_2$—O—$CH_2$—$CH_2$—O—).

1-4C-Alkoxy-1-4C-alkoxy-1-4C-alkyl denotes one of the abovementioned 1-4C-alkoxy-1-4C-alkyl radicals which is substituted by one of the abovementioned 1-4C-alkoxy radicals. An example which may be mentioned is the radical 2-(methoxy)ethoxymethyl ($CH_3$—O—$CH_2$—$CH_2$—O—$CH_2$—).

Fluoro-1-4C-alkoxy-1-4C-alkyl denotes one of the abovementioned 1-4C-alkyl radicals which is substituted by a fluoro-1-4C-alkoxy radical. Here, fluoro-1-4C-alkoxy denotes one of the abovementioned 1-4C-alkoxy radicals which is fully or predominantly substituted by fluorine. Examples of fully or predominantly fluorine-substituted 1-4C-alkoxy which may be mentioned are the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals.

1-7C-Alkyl denotes straight-chain or branched alkyl radicals having 1 to 7 carbon atoms. Examples which may be mentioned are the heptyl, isoheptyl-5-methylhexyl), hexyl, isohexyl-(4-methylpentyl), neohexyl-(3,3-dimethylbutyl), pentyl, isopentyl-(3-methylbutyl), neopentyl-(2,2-dimethylpropyl), butyl, isobutyl, sec-butyl, tert-butyl, propyl, isopropyl, ethyl and methyl radicals.

1-4C-Alkylcarbonyl denotes a radical which, in addition to the carbonyl group, contains one of the abovementioned 1-4C-alkyl radicals. An example which may be mentioned is the acetyl radical.

2-4-C-Alkenylcarbonyl denotes a radical which, in addition to the carbonyl group, contains one of the abovementioned 2-4C-alkenyl radicals. An example which may be mentioned is the ethenylcarbonyl or the 2-propenylcarbonyl radical.

2-4-C-Alkinylcarbonyl denotes a radical which, in addition to the carbonyl group, contains one of the abovementioned 2-4C-alkinyl radicals. An example which may be mentioned is the ethinylcarbonyl or the 2-propinylcarbonyl radical.

Carboxy-1-4C-alkyl denotes, for example, the carboxymethyl (—$CH_2COOH$) or the carboxyethyl (—$CH_2CH_2COOH$) radical.

1-4C-Alkoxycarbonyl-1-4C-alkyl denotes one of the abovementioned 1-4C-alkyl radicals which is substituted by one of the abovementioned 1-4C-alkoxycarbonyl radicals. An example which may be mentioned is the ethoxycarbonylmethyl ($CH_3CH_2OC(O)CH_2$—) radical.

Di-1-4C-alkylamino denotes an amino radical which is substituted by two identical or different of the abovementioned 1-4C-alkyl radicals. Examples which may be mentioned are the dimethylamino, the diethylamino and the diisopropylamino radicals.

1-4C-Alkoxycarbonylamino denotes an amino radical which is substituted by one of the abovementioned 1-4C-alkoxycarbonyl radicals. Examples which may be mentioned are the ethoxycarbonylamino and the methoxycarbonylamino radicals.

1-4C-Alkoxy-1-4C-alkoxycarbonyl denotes a carbonyl group to which one of the abovementioned 1-4C-alkoxy-1-4C-alkoxy radicals is attached. Examples which may be mentioned are the 2-(methoxy)-ethoxycarbonyl ($CH_3$—O—$CH_2CH_2$—O—CO—) and the 2-ethoxy)ethoxycarbonyl ($CH_3CH_2$—O—$CH_2CH_2$—O—CO—) radicals.

1-4C-Alkoxy-1-4C-alkoxycarbonylamino denotes an amino radical which is substituted by one of the abovementioned 1-4C-alkoxy-1-4C-alkoxycarbonyl radicals.

Examples which may be mentioned are the 2-(methoxy) ethoxycarbonylamino and the 2-ethoxy)ethoxycarbonylamino radicals.

2-4C-Alkenyloxy denotes a radical which, in addition to the oxygen atom, contains a 2-4C-alkenyl radical. An example which may be mentioned is the allyloxy radical.

Aryl-1-4C-alkyl denotes an aryl-substituted 1-4-C-alkyl radical. An example which may be mentioned is the benzyl radical.

Aryl-1-4C-alkoxy denotes an aryl-substituted 1-4C-alkoxy radical. An example which may be mentioned is the benzyloxy radical.

Mono- or di-1-4C-alkylamino radicals contain, in addition to the nitrogen atom, one or two of the abovementioned 1-4C-alkyl radicals. Preference is given to di-1-4alkylamino and in particular to dimethyl-, diethyl- or diisopropylamino.

Mono- or di-1-4C-alkylamino-1-4C-alkyl denotes one of the abovementioned 1-4C-alkyl radicals which is substituted by one of the abovementioned mono- or di-1-4C-alkylamino radicals. Preferred mono- or di-1-4C-alkylamino-1-4C-alkyl radicals are the mono- or di-1-4C-alkylaminomethyl radicals. An Example which may be mentioned is the dimethylaminomethyl $(CH_3)_2N—CH_2$ radical.

1-4C-Alkylcarbonylamino denotes an amino group to which a 1-4C-alkylcarbonyl radical is attached. Examples which may be mentioned are the propionylamino $(C_3H_7C(O)NH—)$ and the acetylamino (acetamido, $CH_3C(O)NH—)$ radicals.

Radicals Arom which may be mentioned are, for example, the following substituents: 4-acetoxyphenyl, 4-acetamidophenyl, 2-methoxyphenyl, 3-methoxyphenyl, 4-methoxyphenyl, 3-benzyloxyphenyl, 4-benzyloxyphenyl, 3-benzyloxy-4-methoxyphenyl, 4-benzyloxy-3methoxyphenyl, 3,5-bis(trifluoromethyl)phenyl, 4-butoxyphenyl, 2-chlorophenyl, 3-chlorophenyl, 4-chlorophenyl, 2-chloro-6-fluorophenyl, 3-chloro-fluorophenyl, 2-chloro-5-nitrophenyl, 4-chloro-3nitrophenyl, 3-(4-chlorophenoxy)phenyl, 2,4-dichlorophenyl, 3,4-difluorophenyl, 2,4-dihydroxyphenyl, 2,6-dimethoxyphenyl, 3,4-dimethoxy-5-hydroxyphenyl, 2,5-dimethylphenyl, 3-ethoxy4hydroxyphenyl, 2-fluorophenyl, 4-fluorophenyl, 4-hydroxyphenyl, 2-hydroxy-5-nitrophenyl, 3-methoxy-2-nitrophenyl, 3-nitrophenyl, 2,3,5-trichlorophenyl, 2,4,6-trihydroxyphenyl, 2,3,4-trimethoxyphenyl, 2-hydroxy-1-naphthyl, 2-methoxy-1-naphthyl, 4-methoxy-1-naphthyl, 1-methyl-2-pyrrolyl, 2-pyrrolyl, 3-methyl-2-pyrrolyl, 3,4dimethyl-2-pyrrolyl, 4-(2-methoxycarbonylethyl)-3-methyl-2-pyrrolyl, 5-ethoxycarbonyl-2,4-dimethyl-3-pyrrolyl, 3,4-dibromo-5-methyl-2-pyrrolyl, 2,5-methyl-1-phenyl-3-pyrrolyl, 5-carboxy-3-ethyl-4-methyl-2-pyrrolyl, 3,5-dimethyl-2-pyrrolyl, 2,5-dimethyl-1-(4-trifluoromethylphenyl)-3-pyrrolyl, 1-2,6-dichloro-4-trifluoromethylphenyl)-2-pyrrolyl, 1-(2-nitrobenzyl)-2-pyrrolyl, 1-(2-fluorophenyl)-2-pyrrolyl, 1-(4-trifluoromethoxyphenyl)-2-pyrrolyl, 1-(2-nitrobenzyl)-2-pyrrolyl, 1-(4-ethoxycarbonyl)-2,5-dimethyl-3-pyrrolyl, 5-chloro-1,3-dimethyl-4-pyrazolyl, 5-chloro-1-methyl-3-trifluoromethyl-4-pyrazolyl, 1-(4-chlorobenzyl)-5-pyrazolyl, 1,3-dimethyl-5-(4-chlorophenoxy)-4-pyrazolyl, 1-methyl-3-trifluoromethyl-5-(3-trifluoromethylphenoxy)-4-pyrazolyl, 4-methoxycarbonyl-1-(2,6-dichlorophenyl)-5-pyrazolyl, 5-allyloxy-1-methyl-3-trifluoromethyl-pyrazolyl, 5-chloro-1-phenyl-3-trifluoromethylpyrazolyl, 3,5-dimethyl-1-phenyl-4-imidazolyl, 4-bromo-1-methyl-5-imidazolyl, 2-butyl-imidazolyl, 1-phenyl-1,2,3-triazol-4-yl, 3-indolyl, 4-indolyl, 7-indolyl, 5-methoxy-3-indolyl, 5-benzyloxy-3-indolyl, 1-benzyl-3-indolyl, 2-(4-chlorophenyl)-3-indolyl, 7-benzyloxy-3-indolyl, 6-benzyloxy-3-indolyl, 2-methyl-5-nitro-3-indolyl, 4,5,6,7-tetrafluoro-3-indolyl, 1-(3,5-difluorobenzyl)-3-indolyl, 1-methyl-2-(4-trifluorophenoxy-3-indolyl, 1-methyl-2-benzimidazolyl, 5-nitro-2-furyl, 5-hydroxymethyl-2-furyl, 2-furyl, 3-furyl, 5-(2-nitro-4-trifluoromethylphenyl)-2-furyl, 4-ethoxycarbonyl-5-methyl-2-furyl, 5-(2-trifluoromethoxyphenyl)-2-furyl, 5-(4-methoxy-2-nitrophenyl-2-furyl, 4-bromo-2-furyl, 5-dimethylamino-2-furyl, 5-bromo-2-furyl, 5-sulfo-furyl, 2-benzofuryl, 2-thienyl, 3-thienyl, 3-methyl-2-thienyl, 4-bromo-2-thienyl, 5-bromo-2-thienyl, 5-nitro-2-thienyl, 5-methyl-2-thienyl, 5-(4-methoxyphenyl)-2-thienyl, 4-methyl-2thienyl, 3-phenoxy-2-thienyl, 5-carboxy-2-thienyl, 2,5-dichloro-3-thienyl, 3-methoxy-2-thienyl, 2-benzothienyl, 3-methyl-2benzothienyl, 2-bromo-5-chloro-3-benzothienyl, 2-thiazoly, 2-aminochloro-5-thiazolyl, 2,4-dichloro-thiazolyl, 2-diethylamino-5-thiazolyl, 3-methyl-4-nitro-5-isoxazolyl, 2-pyridyl, 3-pyridyl, 4-pyridyl, 6-methyl-2-pyridyl, 3-hydroxy-5-hydroxymethyl-2-methyl-4-pyridyl, 2,6-dichloro-4-pyridyl, 3-chloro-5-trifluoromethyl-2-pyridyl, 4,6-dimethyl-2-pyridyl, 4-(4-chlorophenyl)-3-pyridyl, 2-chloro-5-methoxycarbonyl-6-methyl-4-phenyl-3-pyridyl, 2-chloro-3-pyridyl, 6-(3-trifluoromethylphenoxy)-3-pyridyl, 2-(4-chlorophenoxy)-3-pyridyl, 2,4-dimethoxy-5-pyrimidine, 2-quinolinyl, 3-quinolinyl, 4-quinolinyl, 2-chloro-3-quinolinyl, 2-chloro-6-methoxy-3-quinolinyl, 8-hydroxy-2-quinolinyl and 4-isoquinolinyl.

Aryl-1-4C-alkoxy-1-4C-alkyl denotes one of the abovementioned 1-4C-alkyl radicals which is substituted by one of the abovementioned aryl-1-4C-alkoxy radicals. Examples which may be mentioned are the benzyloxymethyl, the p-methoxybenzyloxymethyl, p-nitrobenzyloxymethyl and the o-nitrobenzyloxymethyl radical.

Aryl-1-4C-alkylcarbonyl denotes a carbonyl group to which one of the abovementioned aryl-1-4C-alkyl radicals is attached. An example which may be mentioned is the benzylcarbonyl radical.

Aryl-1-4C-alkoxycarbonyl denotes a carbonyl group to which one of the abovementioned aryl-1-4C-alkoxy radicals is attached. An example which may be mentioned is the benzyloxycarbonyl radical.

Suitable salts of compounds of the formula 1 are—depending on the substitution—in particular all acid addition salts. Particular mention may be made of the pharmacologically acceptable salts of the inorganic and organic adds customarily used in pharmacy. Those suitable are water-soluble and water-insoluble acid addition salts with acids such as, for example, hydrochloric acid, hydrobromic acid, phosphoric acid, nitric acid, sulfuric add, acetic acid, citric acid, D-gluconic acid, benzoic acid, 2-(4hydroxybenzyl)benzoic acid, butyric acid, sulfosalicylic add, maleic add, lauric acid, malic acid, fumaric acid, succinic add, oxalic acid, tartaric acid, embonic acid, stearic add, toluenesulfonic add, methanesulfonic add or 3-hydroxy-2-naphthoic acid, where the acids are employed in the salt preparation in an equimolar ratio or in a ratio differing therefrom, depending on whether the acid is a mono- or polybasic acid and on which salt is desired.

It is known to the person skilled in the art that the compounds according to the invention and their salts can, for example when they are isolated in crystalline form, comprise varying amounts of solvents. The invention therefore also embraces all solvates and, in particular, all hydrates of the compounds of the formula 1, and all solvates and, in particular, all hydrates of the salts of the compounds of the formula 1.

One aspect (aspect a) of the invention relates to compounds of the formula 1, in which R1 is hydrogen, 1-4C alkyl, 3-7C-cycloalkyl, 1-4alkoxy-1-4C-alkyl or 1-4C-alkoxycarbonyl R3 is hydroxy-1-4C-alkyl, 1-4C-alkoxy-1-4C-alkyl, 1-4C-alkoxy-1-4C-alkoxy-1-4C-alkyl, 1-4-C-alkoxycarbonyl or the radical —CO—NR31R32, where R31 is hydrogen, 1-7C-alkyl, hydroxy-1-4C-alkyl, 1-4C-alkoxy-1-4C-alkyl or 3-7C-cycloalkyl and R32 is hydrogen, 1-7C-alkyl, hydroxy-1-4C-alkyl, 1-4C-alkoxy-1-4C-alkyl or 3-7C-cycloalkyl, or where R31 and R32 together and including the nitrogen atom to which they are attached are a pyrrolidino, piperidino, morpholino, aziridino or azetidino radical, Arom is a R4-, R5, R6- and R7-substituted mono- or bicyclic aromatic radical selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazotly, pyridinyl, pyrimidinyl, quinolinyl and isoquinolinyl, where R4 is hydrogen, 1-4C-alkyl, hydroxy-1-4C-alkyl, 1-4C-alkoxy, 2-4C-alkenyloxy, 1-4C-alkoxycarbonyl, carboxy-1-4C-alkyl, 1-4C-alkoxycarbonyl-1-4C-alkyl, halogen, aryl, aryl-1-4C-alkyl, aryloxy, aryl-1-4C-alkoxy, trifluoromethyl, nitro, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen or trifluoromethyl, R6 is hydrogen, 1-4C-alkyl or halogen and R7 is hydrogen, 1-4C-alkyl or halogen, PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical $SO_2$—R11 wherein

R8, R9, R10 are independently from each other 1-7C-alkyl, aryl or aryl-1-4C-alkyl, R11 is 1-4C-alkyl or aryl, where aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro, trifluoromethoxy and cyano, and R2 has the meanings as indicated in the outset, and the salts of these compounds.

One embodiment of aspect a (embodiment 1a) relates to those compounds of the formula 1 according to aspect a, in which R2 is hydrogen, 1-4C-alkyl, halogen, 2-4C-alkenyl, 2-4C-alkynyl, hydroxy-1-4C-alkyl, 3-7C-cycloalkyl, 1-4C alkoxycarbonyl, 1-4C-alkylcarbonyl, 2-4C-alkenylcarbonyl, 2-4C-alkinylcarbonyl or the radical —CO—NR21R22, where R21 is hydrogen, 1-4C-alkyl or 1-4C-alkoxy-1-4C-alkyl, R22 is hydrogen, 1-4C-alkyl or 1-4C-alkoxy-1-4C-alkyl, and the salts of these compounds.

A preferred embodiment of aspect a (embodiment 2a) relates to those compounds of the formula 1 according to aspect a, in which R2 is hydrogen, 1-4C-alkyl, halogen, 2-4C-alkenyl, 2-4C-alkynyl, hydroxy-1-4C-alkyl, 3-7C-cycloalkyl, 1-4C-alkoxycarbonyl or the radical —CO—NR21R22, where R21 is hydrogen, 1-4C-alkyl or 1-4C-alkoxy-1-4C-alkyl, R22 is hydrogen, 1-4C-alkyl or 1-4C-alkoxy-1-4C-alkyl, and the salts of these compounds.

A preferred aspect (aspect b) of the invention relates to compounds of the formula 1, in which R1 is 1-4C-alkyl or 3-7C-cycloalkyl Arom is a R4-, R5-, R6 and R7-substituted mono- or bicyclic aromatic radical selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where R4 is hydrogen, 1-4C-alkyl, hydroxy-1-4C-alkyl, 1-4C-alkoxy, 2-4C-alkenyloxy, 1-4C-alkoxycarbonyl, carboxy-1-4C-alkyl, 1-4C-alkoxycarbonyl-1-4C-alkyl, halogen, aryl, aryl-1-4C-alkyl, aryloxy, aryl-1-4C-alkoxy, trifluoromethyl, nitro, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen or trifluoromethyl, R6 is hydrogen, 1-4C-alkyl or halogen and R7 is hydrogen, 1-4C-alkyl or halogen, PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical $SO_2$—R11 wherein

R8, R9, R10 are independently from each other 1-7C-alkyl, aryl or aryl-1-4C-alkyl, R11 is 1-4C-alkyl or aryl where aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro, trifluoromethoxy and cyano, R2 and R3 have the meanings as indicated in the outset and the salts of these compounds.

One embodiment of aspect b (embodiment 1b) relates to those compounds of the formula 1 according to aspect b, in which R2 is 1-4C-alkyl, halogen, hydroxy-1-4C-alkyl, 2-4C-alkenyl, 2-4C-alkynyl, 3-7C-cycloalkyl, 1-4C-alkylcarbonyl, 2-4C-alkenylcarbonyl, 2-4C-alkinylcarbonyl, or the radical —CO—NR21R22,
where
R21 is hydrogen or 1-4C-alkoxy-1-4-alkyl,
R22 is hydrogen or 1-4C-alkoxy-1-4C-alkyl,
R3 is hydroxy-1-4C-alkyl, 1-4C-alkoxy-1-4-alkyl, 1-4C-alkoxy-1-4C-alkoxy-1-4C-alkyl, or the radical —CO—NR31 R32,
where
R31 is hydrogen, 1-7C-alkyl, hydroxy-1-4C-alkyl, 1-4C-alkoxy-1-4C-alkyl or 3-7C-cycloalkyl and
R32 is hydrogen, 1-7C-alkyl, hydroxy-1-4C-alkyl, 1-4C-alkoxy-1-4C-alkyl or 3-7C-cycloalkyl, or where
R31 and R32 together and including the nitrogen atom to which they are attached are a pyrrolidino, piperidino, morpholino, aziridino or azetidino radical, and the salts of these compounds.

Another embodiment of aspect b (embodiment 2b) relates to those compounds of the formula 1 according to aspect b, in which
R2 is 1-4C-alkyl, halogen, hydroxy-1-4C-alkyl, 2-4C-alkenyl, 2-4C-alkynyl, 3-7C-cycloalkyl, 1-4C-alkylcarbonyl, 2-4C-alkenylcarbonyl, 2-4C-alkinylcarbonyl, or the radical —CO—NR21R22,
where
R21 is hydrogen or 1-4C-alkoxy-1-4C-alkyl,
R22 is hydrogen or 1-4C-alkoxy-1-4C-alkyl,
R3 is the radical —CO–NR31R32,
where
R31 is hydrogen, 1-7C-alkyl, hydroxy-1-4C-alkyl, 1-4C-alkoxy-1-4C-alkyl or 3-7C-cycloalkyl and
R32 is hydrogen, 1-7C-alkyl, hydroxy-1-4C-alkyl, 1-4C-alkoxy-1-4C-alkyl or 3-7C-cycloalkyl, or where
R31 and R32 together and including the nitrogen atom to which they are attached are a pyrrolidino, piperidino, morpholino, aziridino or azetidino radical, and the salts of these compounds.

A preferred embodiment of aspect b (embodiment 3b) relates to those compounds of the formula 1 according to aspect b, in which
R2 is 1-4C-alkyl, halogen, hydroxy-1-4C-alkyl, 2-4C-alkenyl, 2-4C-alkynyl, 3-7C-cycloalkyl, or the radical —CO—NR21 R22,
where
R21 is hydrogen or 1-4C-alkoxy-1-4C-alkyl,
R22 is hydrogen or 1-4C-alkoxy-1-4C-alkyl,
R3 is hydroxy-1-4C-alkyl, 1-4C-alkoxy-1-4C-alkyl, 1-4C-alkoxy-1-4C-alkoxy-1-4C-alkyl, or the radical —CO—NR31R32,
where
R31 is hydrogen, 1-7C-alkyl, hydroxy-1-4C-alkyl, 1-4C-alkoxy-1-4C alkyl or 3-7C-cycloalkyl and
R32 is hydrogen, 1-7C-alkyl, hydroxy-1-4C-alkyl, 1-4C-alkoxy-1-4C-alkyl or 3-7C-cylcoalkyl, or where
R31 and R32 together and including the nitrogen atom to which they are attached are a pyrrolidino, piperidino, morpholino, aziridino or azetidino radical, and the salts of these compounds.

A particularly preferred aspect (aspect c) of the invention relates to those compounds of the formula 1, in which
R1 is 1-4C-alkyl,
PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical SO$_2$—R11
wherein
R8, R9, R10 are independently from each other 1-7C-alkyl, aryl or aryl-1-4C-alkyl,
R11 is 1-4C-alkyl or aryl
where
aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro, trifluoromethoxy and cyano,
R2, R3 and Arom have the meanings as indicated in the outset, and the salts of these compounds.

One embodiment of aspect c (embodiment 1c) relates to those compounds of the formula 1 according to aspect c, in which
R2 is 1-4C-alkyl, halogen, hydroxy-1-4C-alkyl, 2-4C-alkenyl, 2-4C-alkynyl, 3-7C-cycdoalkyl, 1-4C-alkylcarbonyl, 2-4C-alkenylcarbonyl, 2-4C-alkinylcarbonyl, or the radical —CO—NR21R22,
where
R21 is hydrogen or 1-4C-alkoxy-1-4C-alkyl,
R22 is hydrogen or 1-4C-alkoxy-1-4C-alkyl,
R3 is hydroxy-1-4C-alkyl, 1-4C-alkoxy-1-4C-alkyl, 1-4C-alkoxy-1-4C-alkoxy-1-4C-alkyl, or the radical —CO—NR31 R32,
where
R31 is hydrogen, 1-7C-alkyl or 3-7C-cycloalkyl
R32 is hydrogen, 1-7C-alkyl or 3-7C-cdoalkyl or where
R31 and R32 together and including the nitrogen atom to which they are attached are a pyrrolidino, piperidino, morpholino, azindino or azetidino radical,
Arom is a R4- and R5-substituted phenyl, pyrrolyl, furanyl (furyl), thiophenyl (thienyl) or pyridinyl,
where
R4 is hydrogen, 1-4C-alkyl, hydroxy-1-4C-alkyl, 1-4C-alkoxy or halogen,
R5 is hydrogen, 1-4C-alkyl, 1-4C-alkoxy or halogen, and the salts of these compounds.

Another embodiment of aspect c (embodiment 2c) relates to those compounds of the formula 1 according to aspect c, in which
R2 is 1-4C-alkyl, halogen, hydroxy-1-4C-alkyl, 2-4C-alkynyl, 1-4C-alkylcarbonyl, 2-4C-alkenylcarbonyl, 2-4C-alkinylcarbonyl, or the radical —CO—NR21R22
where
R21 is hydrogen or 1-4C-alkoxy-1-4C-alkyl,
R22 is hydrogen or 1-4C-alkoxy-1-4C-alkyl,
R3 is the radical —CO—NR31R32,
where
R31 is hydrogen, 1-7C-alkyl or 3-7C-cycloalkyl
R32 is hydrogen, 1-7C-alkyl or 3-7C-cycloalkyl or where
R31 and R32 together and including the nitrogen atom to which they are attached are a pyrrolidino, piperidino, morpholino, aziridino or azetidino radical, Arom is a R4- and R5-substituted phenyl, furanyl (furyl), thiophenyl (thienyl) or pyridinyl,
where
R4 is hydrogen, 1-4C-alkyl, hydroxy-1-4C-alkyl, 1-4C-alkoxy or halogen,
R5 is hydrogen, 1-4C-alkyl, 1-4C-alkoxy or halogen, and the salts of these compounds.

A preferred embodiment of aspect c (embodiment 2c) relates to those compounds of the formula 1 according to aspect c, in which
R2 is 1-4C-alkyl, halogen, hydroxy-1-4C-alkyl, 2-4C-alkenyl, 2-4C-alkynyl, 3-7C-cycloalkyl, or the radical —CO—NR21R22,
where
R21 is hydrogen or 1-4C-alkoxy-1-4C-alkyl,
R22 is hydrogen or 1-4C-alkoxy-1-4C-alkyl,
R3 is hydroxy-1-4C-alkyl, 1-4C-alkoxy-1-4C-alkyl, 1-4C-alkoxy-1-4C-alkoxy-1-4C-alkyl, or the radical —CO—NR31R32,
where
R31 is hydrogen, 1-7C-alkyl or 3-7C-cycloalkyl
R32 is hydrogen, 1-7C-alkyl or 3-7C-cycloalkyl or where
R31 and R32 together and including the nitrogen atom to which they are attached are a pyrrolidino, piperidino, morpholino, aziridino or azetidino radical,
Arom is a R4- and R5-substituted phenyl, pyrrolyl, furanyl (furyl), thiophenyl (thienyl) or pyridinyl,
where
R4 is hydrogen, 1-4C-alkyl, hydroxy-1-4C-alkyl, 1-4C-alkoxy or halogen,
R5 is hydrogen, 1-4C-alkyl, 1-4C-alkoxy or halogen, and the salts of these compounds.

Emphasis is given to an aspect (aspect d) of the invention, which relates to those compounds of the formula 1, in which
R1 is 1-4C-alkyl,
R3 Is the radical —CO—NR31R32,
where
R31 is hydrogen, 1-7C-alkyl or 3-7C-cycloalkyl,
R32 is hydrogen, 1-7C-alkyl or 3-7C-cycloalkyl, or where
R31 and R32 together and including the nitrogen atom to which they are attached are a pyrrolidino, piperidino, morpholino, aziridino or azetidino radical,
Arom is a R4- and R5-substituted phenyl,
where
R4 is hydrogen, 1-4C-alkyl, hydroxy-1-4C-alkyl, 1-4C-alkoxy or halogen,
R5 is hydrogen, 1-4C-alkyl or halogen,
PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical SO$_2$—R11
wherein
R8, R9, R10 are independently from each other 1-7C-alkyl, aryl or aryl-1-4C-alkyl,
R11 is 1-4C-alkyl or aryl
where
aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro, trifluoromethoxy and cyano,
R2 has the meanings as indicated in the outset, and the salts of these compounds.

One embodiment of aspect d (embodiment 1d) relates to those compounds of the formula I according to aspect d, in which
R2 is 1-4C-alkyl, halogen, hydroxy-1-4C-alkyl, 2-4C-alkenyl, 2-4C-alkynyl, 3-7C-cycloalkyl, 1-4C-alkylcarbonyl, 2-4C-alkenylcarbonyl, 2-4C-alkinylcarbonyl or the radical —CO—NR21R22,
where
R21 is hydrogen or 1-4C-alkoxy-1-4C-alkyl,
R22 is hydrogen or 1-4C-alkoxy-1-4C-alkyl, and the salts of these compounds.

Another embodiment of aspect d (embodiment 2d) relates to those compounds of the formula 1 according to aspect d, in which
R2 is 1-4C-alkyl, halogen, hydroxy-1-4C-alkyl, 2-4C-alkynyl, 1-4C-alkylcarbonyl, 2-4C-alkenylcarbonyl, 2-4C-alkinylcarbonyl or the radical —CO—NR21R22
where
R21 is hydrogen or 1-4C-alkoxy-1-4C-alkyl,
R22 is hydrogen or 1-4C-alkoxy-1-4C-alkyl, and the salts of these compounds.

A preferred embodiment of aspect d (embodiment 3d) relates to those compounds of the formula 1 according to aspect d, in which
R2 is 1-4C-alkyl, halogen, hydroxy-1-4C-alkyl, 2-4C-alkenyl, 2-4C-alkynyl, 3-7C-cycloalkyl, or the radical —CO—NR21R22,
where
R21 is hydrogen or 1-4C-alkoxy-1-4C-alkyl,
R22 is hydrogen or 1-4C-alkoxy-1-4C-alkyl, and the salts of these compounds.

Particular emphasis is given to an aspect (aspect a) of the invention, which relates to those compounds of the formula 1, in which
R1 is 1-4C-alkyl,
R3 is the radical —CO—NR31R32,
where
R31 is hydrogen, 1-7C-alkyl or 3-7C-cycdoalkyl,
R32 is hydrogen, 1-7C-alkyl or 3-7C-cycloalkyl, or where
R31 and R32 together and including the nitrogen atom to which they are attached are a pyrrolidino, piperidino, morpholino, aziridino or azetidino radical,
Arom is phenyl.
PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical SO$_2$—R11
wherein
R8, R9, R10 are independently from each other 1-7C-alkyl, aryl or aryl-1-4C-alkyl,
R11 is 1-4C-alkyl or aryl
where
aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro trifluormmethoxy and cyano, R2 has the meanings as indicated in the outset, and the salts of these compounds.

One embodiment of aspect e (embodiment 1e) relates to those compounds of the formula 1 according to aspect e, in which R2 is 1-4C-alkyl, halogen, hydroxy-1-4C-alkyl, 2-4C-alkenyl, 2-4C-alkynyl, 3-7C-cycloalkyl, 1-4C-alkylcarbonyl, 2-4C-alkenylcarbonyl, 2-4C-alkinylcarbonyl or the radical —CO—NR21R22,
where
R21 is hydrogen or 1-4C-alkoxy-1-4C-alkyl,
R22 is hydrogen or 1-4C-alkoxy-1-4C-alkyl, and the salts of these compounds.

Another embodiment of aspect e (embodiment 2e) relates to those compounds of the formula 1 according to aspect e, in which R2 is 1-4C-alkyl, halogen, hydroxy-1-4C-alkyl, 2-4C-alkynyl, 1-4C-alkylcarbonyl, 2-4C-alkenylcarbonyl, 2-4C-alkinylcarbonyl or the radical —CO—NR21R22,
where
R21 is hydrogen or 1-4C-alkoxy-1-4C-alkyl,
R22 is hydrogen or 1-4C-alkoxy-1-4C-alkyl, and the salts of these compounds.

A preferred embodiment of aspect e (embodiment 3e) relates to those compounds of the formula 1 according to aspect e, in which R2 is 1-4C-alkyl, halogen, hydroxy-1-4C-alkyl, 2-4C-alkenyl, 2-4C-alkynyl, 3-7C-cycloalkyl or the radical —CO—NR21R22,
where
R21 is hydrogen or 1-4C-alkoxy-1-4C-alkyl,
R22 is hydrogen or 1-4C-alkoxy-1-4C-alkyl, and the salts of these compounds.

Particular emphasis is given to compounds of the formula 1, where
R1 is 1-4C-alkyl,
R2 is 1-4C-alkyl, halogen or hydroxy-1-4C-alkyl,
R3 is the radical —CO—NR31R32
where
R31 is hydrogen, 1-7C-alkyl or 3-7C-cycloalkyl,
R32 is hydrogen, 1-7C-alkyl or 3-7C-cycloalkyl, or where
R31 and R32 together and including the nitrogen atom to which they are attached are a pyrrolidino radical,
Arom is phenyl,
PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical SO2—R11
wherein
R8, R9, R10 are independently from each other 1-7C-alkyl, aryl or aryl-1-4C-alkyl,
R11 is 1-4C-alkyl or aryl
where
aryl is phenyl or substituted phenyl having one, two or three identical or different substituents from the group consisting of 1-4C-alkyl, 1-4C-alkoxy, carboxyl, 1-4C-alkoxycarbonyl, halogen, trifluoromethyl, nitro, trifluoromethoxy and cyano, and the salts of these compounds.

Particular emphasis is also given to compounds of the formula I where
R1 is 1-4C-alkyl,
R2 is 1-4C-alkyl,
R3 is the radical —CO—NR31R32,
where
R31 is 1-4C alkyl,
R32 is 1-4C-alkyl,
Arom is phenyl,
PG is aryl-1-4C-alkyl or a radical SiR8R9R10
wherein
R8 is 1-7C-alkyl
R9 is 1-7C-alkyl
R10 is 1-7C-alkyl
where
aryl is phenyl, and the salts of these compounds.

The compounds according to the invention can be synthesized from corresponding starting compounds, for example according to the reaction schemes given below. The synthesis is carried out in a manner known to the expert, for example as described in more detail in the examples which follow the schemes.

The compounds of the formula 1 can be prepared for example as outlined in scheme 1, which illustrates processes known to the expert and which use known starting materials.

Protection of the phenolic hydroxy group present in compounds of the formula 2 can be accomplished by standard procedures, which are described for example in T. W. Greene, P. G. M. Wuts, Protective Groups in Organic Synthesis (3$^{rd}$ edition), Wiley, New York, 1999. Suitable protecting groups PG that are to be mentioned are for example ether, ester, sulfonate and silyl ether groups. Examples of protection groups PG which are to be mentioned are methyl, methoxymethyl, benzyloxymethyl, p-methoxybenzyloxymethyl, o-nitrobenzyloxymethyl, p-nitrobenzyloxymethyl, ethoxyethyl, t-butoxymethyl, methoxyethoxymethyl, 2-(trimethylsilyl)-ethoxymethyl, tetrahydropyranyl, tetrahydrofuranyl, t-butyl, benzyl, p-methoxybenzyl, o-nitrobenzyl, p-nitrobenzyl, 2,6-dimethylbenzyl, cyclohexyl, trimethylsilyl, triethylsilyl, triisopropylsilyl, dimethylisopropylsilyl, diethylisopropylsilyl, dimethylthexylsilyl, t-butyldimethylsilyl, t-butyidiphenylsilyl, tribenzylsilyl, triphenylsilyl, diphenylmethylsilyl, pivaloate, benzoate, mesitoate, t-butyl carbonate, methanesulfonate or toluenesulfonate radicals.

The compounds of the formula 1 can be obtained from corresponding compounds of the formula 3 by methods known to the expert, for example by an asymmetric reduction, which can be preformed for example as an asymmetric catalytic reduction.

The invention thus further relates to a process for the preparation of compounds of the formula 1, in which R1, R2, R3, Arom and PG have the meanings as indicated in the outset, which comprises an asymmetric reduction of compounds of the formula 3, in which R1, R2, R3, Arom and PG have the meanings as indicated in the outset.

The invention thus further relates to a process for the preparation of compounds of the formula 1, in which R1, R2, R3, Arom and PG have the meanings as indicated in the outset, which comprises an asymmetric catalytic reduction of compounds of the formula 3, in which R1, R2, R3, Arom and PG have the meanings as indicated in the outset One example of such an asymmetric catalytic reduction to be emphasized is the asymmetric catalytic hydrogenation reaction. A great variety of catalysts is available for this kind of transformation (see for example the following literature: Chem. Rev. 2003, 103, 3029-3069; Eur. J. Org. Chem. 2003, 10, 1931-1941; Synthesis 2003, 11, 1639-1642; Chem. Eur. J. 2003, 9, 2953-2962; Angew. Chem. 2001, 113, 40-75).

Active hydrogenation catalysts suitable for the above mentioned transformation can be derived from precatalysts which are characterized by the formula $MD_mX_nP_oL_p$, wherein M is a transition metal, preferably rhodium (Rh), ruthenium (Ru) or iridium (Ir);

D is a π-donor ligand, like for example an olefin, arene, or cyclopentadiene;

X is an anionic heteroatom ligand, like for example carboxyl, 1-4C-alkoxy, hydroxyl or preferably halogen, especially chlorine;

P is a chiral ligand, preferably a chiral phosphorus ligand, especially a chiral diphosphine or a chiral aminophosphine ligand;

L is an additional donor ligand, like for example a phosphine or preferably an amine or a chiral diamine; and m, n, o, pare 0, 1, 2, 3.

These precatalysts are preferably used as isolated species (see for example Angew. Chem. 1998, 110, 1792-1796) or can be prepared in situ by mixing one or more of the ligands with the corresponding metal precursor (see for example J. Am. Chem. Soc. 1995, 117, 2675-2676). Examples of metal precursors that are to be mentioned are [Rh(cod)Cl]$_2$, [Rh(nbd)Cl]$_2$, [Rh(cp*)Cl$_2$]$_2$ [Ru(cod)(2-methylallyl)$_2$], [Ru$_2$Cl$_4$(benzene)$_2$], [RuCl$_2$(p-cymene)]$_2$, [RuCl$_2$(PPh$_3$)$_2$], [Ir(cod)Cl]$_2$, wherein the following abbreviations are used: cod=cyclooctadiene, nbd=norbornadiene, cp*=pentamethylcyclopentadienyl.

A great variety of chiral phosphorus ligands P is known to the expert which can be used in active hydrogenation catalysts mentioned above in the catalytic asymmetrical hydrogenation of aromatic ketones (see for example Chem. Rev. 2003, 103, 3029-3069 or Synthesis 2003, 11, 1639-1642).

One class of chiral phosphorus ligands P particularly suitable for the catalytic asymmetrical hydrogenation of aromatic ketones are chiral diphosphine ligands, among which the following ligands are to be mentioned:
2,2'-Bis(diphenylphosphanyl)-1,1'-binaphthyl (BINAP), 2,2'-Bis(di-4-tolylphosphanyl)-1,1'-binaphthyl (ToIBINAP), 2,2'-Bis(di-3,5-xylylphosphanyl)-1,1'-binaphthyl (XylBINAP), 2,3-Bis(diphenylphosphanyl)butan (CHIRAPHOS), 2,3-O-Isopropyliden-2,3-dihydroxy-1,4-bis(diphenylphosphanyl)butan (DIOP)
2,4-Bis(diphenylphosphino)pentane (BDPP), P,P'-1,2-phenylene-bis[2,5-dimethyl-7-phosphabicyclo [2.2.1]heptane], (Me-PennPhos), 2,2'-Bis(diphenylphosphanyl)-1, 1'-dicydopentane (BICP), 4,12-Bis(di(3,5-xylyl) phosphino)[2.2]-paracyclophane (Xylyl-PHANEPhos), 2,2',6,6'-Tetramethoxy-4,4'-bis(di(3,5-xylyl)phosphino)-3,3'-bipyridine (Xylyl-P-Phos), 2,2'-Bis(diphenylphosphanyly)-1,1'-biphenyl (BiPhep).

A further class of chiral phosphorus ligands P particularly suitable for the catalytic asymmetrical hydrogenation of aromatic ketones are aminophosphine ligands, among which the following ligands are to be mentioned:
2-2-Diphenylphosphanylferrocenyl)-4-isopropyl-4,5-dihydro-oxazole,2-(2-Diphenylphosphanylferrocenyl) -4-tert-butyl-4,5-dihydro-oxazole, 2-(2-Diphenylphosphanylferrocenyl)-4-phenyl-4,5-dihydro-oxazole, 2-{2-[Bis-3,5-dimethylphenyl)-phosphanyl]-ferrocenyl}-4-isopropyl-4,5-dihydro-oxazole and 2-{2-[Bis-(3,5-bis-trifluoromethylphenyl)-phosphanyl]-ferrocenyl}-4-isopropyl-4,5-dihydro-oxazole, 2-(2-Diphenylphosphanyl-thiop -3yl)-4-isopropyl-4,5-dihydro-oxazole, 4-Benzyl-2-(3-diphenylphosphanyl-benzo[b]thophen-2-yl)-4,5-dihydro-oxazole, 2-(2-Diphenylphosphanyl-phenyl)-4-isopropyl-4,5-dihydro-oxazole and 2-(4-Diphenylphosphanyl-2,5-dimethyl-thiophen-3-yl)-4-isopropyl-4,5dihydro-oxazole.

In addition to the chiral phosphorus ligands P mentioned above, the hydrogenation catalyst can contain one or more additional donor ligands L, (like for example phosphine or amine ligands. Phosphine ligands L which are to be mentioned are trimethylphosphine, triethylphosphine, tributylphosphine, tricyclohexylphosphine, tri(p-tolyl)phosphine, diphenylmethylphosphine, dimethylphenylphosphine, bis-diphenylphosphinoethane, bis-diphenylphosphino-propane, bis-diphenylphosphinobutane, bis-dimethylphosphinoethane, bis-dimethylphosphinopropane and especially triphenylphosphine. Amine ligands L which are to be mentioned are methylamine, ethylamine, propylamine, butylamine, pentylamine, hexylamine, cyclopentylamine, cyclohexylamine, benzylamine, dimethylamine, diethylamine, dipropylamine, dihexylamine, dicyclopentylamine, dicyclohexylamine, dibenzylamine, diphenylamine, trimethylamine, triethylamine, tripropylamine, tributylamine, tripentylamine, trihexylamine, tricyclopentylamine, tricydohexylamine, tribenzylamine, phenylethylamine, triphenylamine, methylenediamine, ethylenediamine, 1,2-diaminopropane, 1,3-diaminopropane, 1,4diaminobutane, 2,3-diaminobutane, 1,2-cyclopentanediamine, 1,2-cyclohexanediamine N-methylethylenediamine, N,N'-dimethylethylenediamine, N,N,N'-trimethylethylenediamine, N,N,N',N'-tetramethylethylenediamine, o-phenylenediamine and p-phenylenediamine. Chiral amine ligands L which are to be emphasized are 1,2-Diphenylethylendiamin (DPEN), 1,1-Di(4-anisyl)-2-isobutyl-1,2-ethylendiamin (DAIBEN), 1,1-Di(4-anisyl)-2-isopropyl-1,2-ethylendiamin (DAIPEN), or 1,1-Di(4-anisyl)-2-methyl-1,2-ethylendiamin (DAMEN), and Cyclohexan-1,2-diamin. These chiral amine ligands L are preferably used in combination with chiral diphospine ligands P in the active hydrogenation catalysts.

Effective asymmetric reduction of prochiral ketones can be achieved using these precatalysts. The optimization of the reaction conditions (temperature, hydrogen pressure, solvent) and the choice of additives (for example inorganic or organic bases like KOH, NaOH, $K_2CO_3$, KO$^t$Bu) can be accomplished by the person skilled in art.

Particularly suitable for the asymmetric catalytic hydrogenation of compounds of the formula 3 to compounds of the formula 1 are the active hydrogenation catalysts described for example in the European Patent EP 0718265, in the Patent Application WO 04/050585 and in Angew. Chem. 2001, 113, 40.

Exemplary hydrogenation catalysts, which are particularly preferred to transform ketones of the formula 3 into alcohols of the formula 1 are the complexes $RuCl_2[(S)BINAP][(S)-DAIPEN]$, $RuCl_2[(S)-Xyl-P-Phos][(S)-DAIPEN]$, $RuCl_2[(S)-Xyl-BINAP][(S)-DAIPEN]$, $RuCl_2[BiPhep][(S)-DAIPEN]$, and $(RuCl_2[(S)-TolBINAP])_2$ ($Et_3N$) and especially $RuCl2(PPh_3)[2-(2-(S_m)-diphenylphosphanylferracenyl)-4(S)-isopropyl-4,5-dihydrooxazole]$ (known from WO 04/050585).

Alternatively, prochiral ketones can be reduced by transfer hydrogenation (see for example Tetrahedron: Asymm. 1999, 10, 2045-2061). Using this method, small organic molecules, like for example isopropanol or formic add, serve as hydrogen source. Suitable precatalysts, which can be used for this transformation, are described by the formula $M'D'_mX'_nA'_o$, wherein M is a transition metal, preferably rhodium (Rh), ruthenium (Ru) or iridium (Ir);

D' is a π-donor ligand, like for example an olefin, arene, or cyclopentadiene;

X' is an anionic heteroatom ligand, like for example carboxyl, 1-4C-alkoxy, hydroxyl or preferably halogen, especially chlorine;

A' is a chiral ligand, for example a phosphine, bipyridine, phenanthroline, tetrahydrobioxazole, diamine, polyurea, diimine or preferably a phosphinooxazoline, monosulfonated diamine, β-aminoalcohol, aminophosphine (for representative examples see for example Tetrahedron: Asymm. 1999, 10, 2045-2061 or WO 04/050585)

and m, n, o are 0, 1, 2, 3.

These precatalysts are preferably used as isolated species or can be prepared in situ by mixing the ligands with the corresponding metal precursor. Examples for metal precursors that might be mentioned are $[Rh(cod)Cl]_2$, $[Rh(nbd)Cl]_2$, $[Rh(cp*)Cl_2]_2$ $[Ru(cod)(2-methylallyl)_2]$, $[Ru_2Cl_4(benzene)_2]$, $[RuCl_2(p-cymene)]_2$, $[RuCl_2(PPh_3)_2]$, $[Ir(cod)Cl]_2$, wherein the following abbreviations are used: cod=cydooctadiene, nbd=norbornadiene, cP*=pentamethylcyclopentadienyl.

Effective asymmetric reduction of prochiral ketones can be achieved using these precatalysts. The optimization of the reaction conditions (temperature, hydrogen source, solvent) and the choice of additives (for example inorganic or organic bases like KOH, NaOH, $K_2CO_3$, KO$^t$Bu) can be accomplished by the person skilled in art.

Further methods to perform the asymmetric reduction mentioned above are known to the expert and are described for example in E. N. Jacobsen, k Pfaltz, H. Yamamoto, Comprehensive Asymmetric Catalysis, Vol. I-III, Springer, Berlin, 1999. These methods include the reduction of prochiral ketones using chiral reducing agents, for example chiral boranes, preferably diisopinocampheylchloroborane, as disclosed for example in Aidrichimica Acta 1987, 20(1), 9-24.

Alternatvely, an achiral reducing agent in the presence of a chiral auxiliary or a chiral catalyst can be employed. Examples for achiral reducing agents that might be mentioned are borane (available as complex with dimethyl sulfide, THF, 1,4-thioxane, phenylamine) or catecholborane. Chiral auxiliaries include—among many others—enantiopure diphenyl-pyrrolidin-2-yl-methanol or oxazaborolidines (see for example Angew. Chem., Int Ed. Engl. 1998, 37, 1986-2012).

Another method to reduce prochiral ketones in an asymmetric manner is the hydrosilylation reaction. Typically, an achiral silane (for example tiethylsilane, dimethylphenylsilane or methyidiphenylsilane) is used in combination with a chiral catalyst. One of the many possibilities to obtain suitable chiral catalysts is the combination of Rhodium complexes (for example {Rh(cyclooctadiene)Cl}$_2$ or {RhCl(ethylene)$_2$}$_2$ with chiral phosphanes (see for example Angew. Chem. 2002, 114(20), 4048-4050 or Angew. Chem. 2003, 115(11), 1325-1327).

Alternatively, enzymatic methods might be used for the reduction of prochiral ketones (see for example Chem. Rev. 1992, 92, 1071-1140, Tetrahedron: Asymm. 2003, 14, 2659-2681). Examples for biological systems that might be mentioned are baker's yeast (Synthesis 1990, 1-25), alcohol dehydrogenases from baker's yeast, *Pseudomonas* sp. Strain PED (J. Org. Chem. 1992, 57, 1526-1532), *L. kefir* (J. Org. Chem. 1992, 57, 1532-1536), *G. candidum*, or *Rhodococcus rubber* (J. Org. Chem. 2003, 68, 402-406).

Cleavage of the protecting group PG present in compounds of the formula 1 can be accomplished using standard methods, described for example in T. W. Greene, P. G. M. Wuts, Protective Groups in Organic Synthesis (3$^{rd}$ edition), Wiley, New York, 1999. The deprotected diols of the formula 4 are valuable precursors for the synthesis of enantiomerically pure 7H-8,9-dihydro-pyrano[2,3-c]imidazo-[1,2-a]pyridines of the general formula 5, as shown in a general way in the following scheme 2.

Scheme 2:

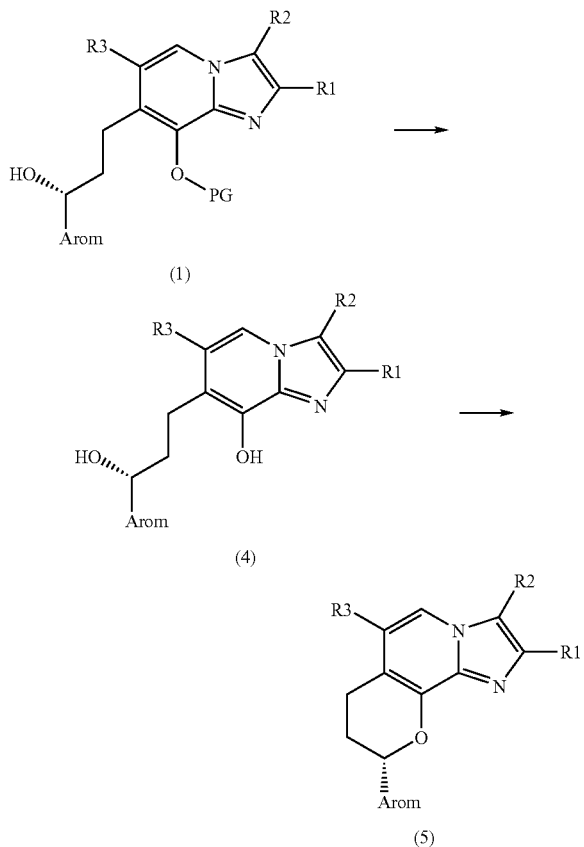

The cyclization step is carried out under conditions known to the expert Suitable reaction conditions are inter alia Mitsunobu conditions, for example using DIAD (diisopropyl azodicarboxylate) in the presence of triphenylphosphine. The enantiomeric excess of the starting material of the formula 1 can thus be transferred to pharmaceutically active compounds of the formula 5 with the preferred stereochemical configuration of the Arom radical.

The invention thus further relates to the use of compounds of the formula 1, in which R1, R2, R3, Arom and PG have the meanings as indicated in the outset, for the preparation of compounds of the formula 4 and their salts, in which R1, R2, R3 and Arom have the meanings as indicated in the outset Furthermore the invention relates to the use of compounds of the formula 1, in which R1, R2, R3, Arom and PG have the meanings as indicated in the outset, for the preparation of compounds of the formula 5 and their salts, in which R1, R2, R3 and Arom have the meanings as indicated in the outset Compounds of the formula 2 are known for example from WO 03/014123, or they can be prepared in a known manner, analogously to known compounds. In contrast to WO 03/014123 a further purification step of compounds of the formula 2 is required prior to conversion to compounds of the formula 3, because the purity of the compounds of the formula 3 has a major impact on the reaction conditions and the outcome of the asymmetric catalytic hydrogenation. Compounds of the formula 2 can be purified for example by a crystallization step in the presence of a suitable organic acid, as described in an exemplary manner in the examples. Alternatively, compounds of the formula 3 can be purified by other methods known to the expert.

One advantage of performing the asymmetric catalytic reduction on the stage of compounds of the formula 3 instead of compounds of the formula 2 is that the introduction of the protecting group PG allows the use of a larger variety of hydrogenation catalysts, such as catalysts which are not compatible with certain functional groups, like for example polar and/or chelating groups in the substrate, like for example an aromatic hydroxy functionality which is present in compounds of the formula 2.

Another advantage of performing the asymmetric catalytic reduction on the stage of compounds of the formula 3 instead of compounds of the formula 2 is that by the introduction of a suitable protecting group PG the solubility of the substrates for the asymmetric catalytic reduction in the solvent used for carrying out the reduction can be increased. Otherwise unsoluble or only slightly soluble compounds of the formula 2 can more conveniently be subjected to the reduction described above if they are first transformed to compounds of the formula 3, which transformation can render these compounds more soluble in solvents generally used in reduction reactions described above.

EXAMPLES

The examples below serve to illustrate the invention in more detail without limiting it. Further compounds of the formula 1 whose preparation is not described explicitly can likewise be prepared in an analogous manner or in a manner known per se to the person skilled in the art, using customary process techniques. The abbreviation ee stands for enantiomeric excess, v for volume. For the assignment of NMR signals, the following abbreviations are used: s (singlet), d (duplet), t (triplet), q (quartet), $m_c$ (mutfiplet centred), b (broad). The following units are used: ml (millilitre), l (litre), nm (nanometer), mm (millimeter), mg (milligramme), g (gramme), mmol (millimol), N (normal), M (molar), min (minute), MHz (megahertz).

Furthennore the following abbreviations are used for the chemical substances indicated:

| DMF | dimethylformamide |
|---|---|
| Thexyl | 1,1,2-trimethylpropyl |
| THF | tetrahydrofuran |

All of the HPLC columns used for preparative and analytical purposes are commercially available:
CHIRALPAK® AD-H, CHIRALCEL® ODH: DAICEL Chemical Industries Ltd, Tokyo or Chiral Technologies-Europe SARL, Ilkirch, France
XTerra RP 18: Waters Corporate, Milford, Mass., USA.

Compounds of the Formula 1

1. 8Benzyloxy-7-[(3R)-3-hydroxy-3-phenyl-propyl]-2,3-dimethyl-imidazol[1,2a]pyridine-6-carboxylic acid dimethylamide Route A: A flame-dried flask filled with argon was charged with toluene (180 ml), which had been thoroughly degassed with argon. The ketone 8-benzyloxy-2,3-dimethyl-7-(3-oxo-3-phenyl-propyl)-imidazo[1,2-a]pyridine-6-carboxylic acid dimethylamide (2.30 g, 5.0 mmol) was added and stirring was continued until a clear solution was obtained (approximately 10 minutes). After addition of the hydrogenation catalyst RuCl$_2$(PPh$_3$)[2-(2-(S$_m$)-diphenylphosphanylferrocenyl)-4-(S)-isopropyl-4,5-dihydro-oxazole] (220 mg, 0.25 mmol, 5 mol-%) stirring was continued for another 20 minutes. The obtained red-brown solution was treated with 1 N sodium hydroxide solution (60 ml), which had been degassed with argon prior to use. Under inert conditions, the biphasic mixture was transferred to a 1 l steel autoclave equipped with a glass inlay, which had been filled with argon. The autoclave was purged with argon and a hydrogen pressure of 80 bar was applied. After a reaction time of 3 days at 40° C. the mixture was removed from the autoclave and a pH-value of 8 was adjusted by addition of 6 N hydrochloric acid. The phases were separated and the aqueous phase was extracted with ethyl acetate (2×15 ml). The combined organic phases were washed with water (40 ml), dried over sodium sulfate, and concentrated in vacuo. The residue (6 g of a green oil) was purified by flash chromatography [80 g of silica gel, eluant dichloromethane/methanol=100:3 (v/v)]. A green, foamy solid was isolated which was dried in vacuo. The title compound (2.2 g) was obtained in 96% yield (melting point 52-54° C.) and was pure by means of $^1$H-NMR spectroscopy. The optical purity of the title compound was determined by chiral HPLC (enantiomeric excess: 78%).

$^1$H-NMR (200 MHz, dmso-d$_6$): δ=1.73 (m$_c$, 2H), 2.34, 2.35 (2 s, 6H), 2.49 (m$_c$), 2.74, 2.91 (2 s, 6H), 4.46 (m$_c$, 1H), 5.16 (d, 1H), 5.61 (s, 2H), 729 (m$_c$, 10H), 7.87 (s, 1H).

Conditions for the HPLC-separation of the enantiomers: Chiral column: Chiralcel OD-H 250×4.6 mm, 5 μm.—Eluant 90% n-hexane/10% isopropanol.—Flow: 1 ml/min.—Temperature: 30° C.—Diode array detection at 220, 240, and 254 nm.—Retention time (3R)-enantiomer: 22.7 min/87.8, 88.6, 88.6 area-%. —Retention time (3S)-enantiomer: 28.3 min/10.7, 10.5, 10.5 area-%

Route B: In a flame-ddied flask filled with argon, the ketone 8-benzyloxy-2,3-dimethyl-7-(3-oxo-3-phenyl-propyl)-imidazo[1,2-a]pyridine-6carboxylic add dimethylamide (4.00 g, 8.8 mmol) was suspended in dry isopropanol (400 ml) which had been degassed with argon. Potassium tert-butylate (1.20 g, 9.8 mmol) was added to the stirred suspension, at which point a yellow solution was obtained. The hydrogenation catalyst RuCl$_2$[(S)-BINAP][(S)-DAIPEN] (100 mg, 0.09 mmol, 1 mol-%) was added next and stirring was continued for 20 minutes. Under inert conditions, the reaction mixture was transferred to a 1 l steel autoclave equipped with a glass inlay, which had been filled with argon. The autoclave was purged with argon and a hydrogen pressure of 40 bar was applied. After a reaction time of 22 hours at room temperature, the reaction mixture (a yellow solution) was removed from the autoclave and concentrated to a volume of 80 ml. The residue was diluted with ice water (100 ml) and dichloromethane (120 ml) and a pH-value of 8 was adjusted by addition of 2 N hydrochloric acid. The phases were separated and the aqueous phase was extracted with dichloromethane (3×30 ml). The combined organic phases were washed with water (30 ml), dried over sodium sulfate, and concentrated in vacuo. The residue was purified by flash chromatography [200 g of silica gel, eluant dichloromethane/methanol=100:3 (v/v)]. A green oil was isolated which solidified upon drying in vacuo. The title compound (32 g) was obtained in 79% yield (green foamy solid, melting point 58-60° C.) and was pure by means of $^1$H-NMR spectroscopy. The optical purity of the title compound was determined by chiral HPLC (enantiomeric excess: 74-75%).

$^1$H-NMR (200 MHz, dmso-d$_6$): δ=1.73 (m$_c$, 2H), 2.34, 2.35 (2 s, 6H), 2.49 (m$_c$), 2.74, 2.91 (2 s, 6H), 4.46 (m$_c$, 1H), 5.16 (d, 1H), 5.61 (s, 2H), 7.29 (m$_c$, 10H), 7.87 (s, 1H).

Conditions for the HPLC-separation of the enantiomers: Chiral column: Chiralcel OD-H 250×4.6 mm, 5 μm.—Eluant 90% n-hexane/10% isopropanol.—Flow: 1 ml/min.—Temperature: 30° C.—Diode array detection at 220, 240, and 254 nm.—Retention time (3R)-enantomer: 25.6 min 184.6, 84.3, 84.9 area-%. —Retention time (3S)-enantiomer: 31.8 min/12.3, 12.4, 122 area-%

2. 8-[Dimethyl-(1,1,2-trimethyl-propyl)-silanyloxy]-7-[(3R)-3-hydroxy-3-phenyl-propyl]-2,3-dimethyl-imidazo[1,2-a]pyridine-6-carboxylic acid dimethylamide In a flame-dried flask filled with argon, the ketone 8-[dimethyl-(1,1,2-trimethyl-propyl)-silanyloxy]-2,3-dimethyl-7-(3-oxo-3-phenyl-propyl)-imidazo[1,2-a]pyridine-6-carboxylic acid dimethylamide (2.55 g, 5.0 mmol) was dissolved in toluene (180 ml), which had been thoroughly degassed with argon. The hydrogenation catalyst RuCl$_2$(PPh$_3$)[2-(2-(S$_m$)diphenylphosphanylferrocenyl)-4(S)-isopropyl-4,5-dihydro-oxazole](220 mg, 0.25 mmol, 5 mol-%) was added and the mixture was stirred for 30 minutes at room temperature. The obtained red-brown solution was treated with 1 N sodium hydroxide solution (60 ml), which had been degassed with argon prior to use. Under inert conditions, the biphasic mixture was transferred to a 1 l steel autoclave equipped with a glass inlay, which had been filled with argon. The autodave was purged with argon and a hydrogen pressure of 80 bar was applied. After a reaction time of 3 days at 40° C. the mixture was removed from the autodave and a pH-value of 8 was adjusted by addition of 2 N hydrochloric acid. The phases were separated and the aqueous phase was extracted with ethyl acetate (2×20 ml). The combined organic phases were washed with water (2×20 ml), dried over sodium sulfate, and concentrated in vacuo. The residue (4 g of a green oil) was purified by flash chromatography [60 g of silica gel, eluant ethyl acetate/petrol ether=8:2 (v/v)]. A green oil was isolated which solidified upon drying in vacuo. The title compound (2.2 g) was obtained in 86% yield. The foamy solid showed a melting point of 56-58° C. and was pure by means of $^1$H-NMR spectroscopy. The optical purity of the title compound was determined by chiral HPLC (enantiomeric excess: 88%).

$^1$H-NMR (200 MHz, dmso-d$_6$): δ=0.32 (s, 6H), 0.93 (d, 6H), 0.97 (s, 6H), 1.81 (m$_c$, 3H), 2.27 (s, 3H), 2.32 (s, bs, 4H), 2.65 (bm$_c$, 1H), 2.78, 2.92 (2 s, 6H), 4.49 (m$_c$, 1H), 5.17 (d, 1H), 7.28 (m$_c$, 5H), 7.73 (s, 1H).

Conditions for the HPLC-separation of the enantiomers: Chiral column: Chiralcel OD-H 250×4.6 mm, 5 μm.—Eluant 95% n-hexane 15% isopropanol.—Flow: 1 ml/min.—Temperature: 35° C.—Diode array detection at 220 and 254 nm.—Retention time (3R)-enantiomer: 11.3 min/92.7, 93.8 area-%.—Retention time (3S)-enantiomer: 18.7 min/5.7, 5.9 area-%.

Starting Materials

A. 8-Hydroxy-2,3-dimethyl-7-(3-oxo-3-phenyl-propyl)-imidazo[1,2a]pyridine-6-carboxylic acid dimethylamide (a) In a flame-dried flask filled with argon, a suspension of the alcohol 8-hydroxy-2,3-dimethyl-imidazo[1,2-a]pyridine-6-carboxylic acid dimethylamide (50.0 g, 214 mmol) in dry dichloromethane (1.2 l) was treated with N,N-dimethylmethyleneiminium iodide (40.3 g, 218 mmol). The reaction mixture was stirred for 1 hour at room temperature. In the beginning, a clear solution was obtained, within 10 minutes the formation of a precipitate was observed. The solvent was then removed under reduced pressure.

(b) The rotary evaporator was filled with argon, the colourless solid (7-dimethylaminomethyl-6-dimethylcarbamoyl-8-hydroxy-2,3-dimethyl-imidazo[1,2-a]pyridin-1-ium iodide) was dried in vacuo, and was dissolved in dry DMF (1.1 l) which had been pre-heated to 50° C. An almost clear solution was obtained, which was treated with potassium carbonate (30.4 g, 220 mmol) and 1-(1-phenyl-vinyl)-pyrrolidine (CAS 3433-56-5, 82.5 g, purity: 90 weight-%, 428 mmol). In a pre-heated oil bath, the brown solution was stirred for 30 minutes at 50° C. and was then poured onto a stirred mixture of ammonium chloride (130 g), water (200 ml), ice (300 g), and dichloromethane (600 ml). Stirring was continued for several minutes and the pH-value was adjusted to pH=8 by addition of 6N hydrochloric acid. The phases were separated and the aqueous phase was extracted with dichloromethane (3×100 ml). The combined organic phases were washed with water (2×100 ml), dried over sodium sulfate and concentrated under reduced pressure (DMF was removed at a temperature of 60° C.). A dark-brown oily residue (80 g) was obtained which was dried in vacuo.

(c) The residue (crude title compound) was purified by filtration over silica gel [500 g, eluant ethyl acetate (removal of acetophenone formed by cleavage of excess enamine), then ethyl acetate/methanol=8:2 (v/v)]. A redbrown solid was isolated (60 g of crude title compound, HPLC-purity: 88.08%) which was dried in vacuo, dissolved in methanol (200 ml), and treated with fumaric acid (25.5 g, 220 mmol). The brown suspension was stirred for 20 minutes at 40° C., at which point a clear solution was obtained. The solution was concentrated under reduced pressure until a dense suspension was formed. Acetone (120 ml) was added and the mixture was concentrated again until a dense suspension was formed. The slurry was diluted with acetone (150 ml) and was stirred at 40° C. (30 minutes), room temperature (19 hours), and at 0° C. (2 hours). The precipitate, which was formed, was removed by filtration, washed with acetone (20 ml) and diethyl ether (50 ml), and dried in vacuo. A colourless solid (51 g, 49% yield, melting point 196-198° C., HPLC-purity 98.24%) was obtained which was characterized by $^1$H-NMR spectroscopy as the salt of the title compound and fumaric acid in a molar ratio of 1:1.

(d) The salt of the title compound and fumaric acid (50 g, 104 mmol) was added portion-wise to a mixture of sodium bicarbonate (42 g, 500 mmol), water (400 ml), and dichloromethane (400 ml). The biphasic mixture was stirred for 5 minutes. The phases were separated and the aqueous phase was extracted with dichloromethane (2×50 ml). The organic phases were washed with water (2×100 ml), dried over sodium sulfate and concentrated under reduced pressure. A colourless, foamy solid was isolated, which was characterized as the title compound (37.7 g, 99% yield, 49% overall yield). The sample was pure by means of $^1$H-NMR spectroscopy and showed an HPLC purity of 99.07%.

$^1$H-NMR (CDCl$_3$, 200 MHz): δ=2.32, 2.37 (2 s, 6H), 2.95 (s), 3.05 (bs), 3.14 (s, Σ8H), 3.42 (m$_c$, 2H), 7.29 (s, 1H), 7.47 (m$_c$, 3H), 8.00 (m$_c$, 2H).

Conditions for the determination of purity by HPLC: Column: 150×4.6 mm XTerra RP 18 5 μm.—Eluant 0.01 M KH$_2$PO$_4$ (pH 2.0)/acetonitrile/water 90:10:0 (v/v/v) [0 min] to 15:80:5 (v/v/v) [30 min].—Flow: 1.0 ml/min.—Temperature: 30° C.—Diode array detection at 245 nm.—Retention time: 9.4 min/99.07 area-%.

B. 8-Benzyloxy-2,3-dimethyl-7-(3-oxo-3-phenyl-propyl)-imidazo[1,2-a]pyridine-6-carboxylic acid dimethylamide In a flame-dried flask filled with argon, the hydroxyketone 8-hydroxy-2,3-dimethyl-7-(3-oxo-3-phenyl-propyl)-imidazo[1,2-a]pyridine-6-carboxylic acid dimethylamide (5.00 g, 13.7 mmol) was suspended in dry DMF (100 ml). The stirred mixture was treated with potassium carbonate (1.90 g, 13.7 mmol) and benzyl chloride (slow addition of 1.50 ml, 1.65 g, 13.0 mmol). A light-green suspension was obtained which was heated to 55° C. After a period of 5 hours, the reaction mixture was cooled to 0° C. and poured onto a stirred mixture of saturated ammonium chloride solution (200 ml) and dichloromethane (350 ml). Stirring was continued for several minutes, the phases were separated, and the aqueous phase was extracted with dichloromethane (2×50 ml). The combined organic phases were washed with water (2×50 ml), dried over sodium sulfate, and concentrated under reduced pressure. The residue, 10 g of a dark-green sticky oil, was purified by flash chromatography (180 g of silica gel, eluant ethyl acetate). A colourless solid (6.0 g, 96% yield) was isolated which was treated with acetone (15 ml). The suspension was filtered. The residue was washed with acetone (3 ml) and diethyl ether (10 ml) and dried in vacuo applying a temperature of 40° C. Colourless crystals of the the compound (3.2 g, 51% yield) were obtained which showed a melting point of 156-158° C. and were pure by HPLC and $^1$H-NMR analysis.

$^1$H-NMR (200 MHz, dmso-d$_6$): δ=2.36, 2.39 (2 s, 6H), 2.77, 2.84 (m$_c$, s, Σ5 H), 2.98, 3.01 (s, m$_c$, Σ5H), 5.73 (s, 2H), 7.32 (m$_c$, 5H), 7.49 (t, 2H), 7.63 (t, 1H), 7.85 (d, 2H), 7.96 (s, 1H).

Conditions for the determination of purity by HPLC: Column: XTerra RP 18 150×4.6 mm 5 μm.—Eluant 0.01 M KH$_2$PO$_4$ buffer (pH 2)/CH$_3$CN/H$_2$O—Gradient 90:10:0 (0 min) to 15:80:5 (30 min).—Flow: 1 ml/min.—Temperature: 30° C.—Diode array detection at 245 nm—Retention time: 14.5 min /99.79 area-%.

C. 8-[Dimethyl-(1,1,2-trimethyl-propyl)-silanyloxy]-2,3-dimethyl-7-(3-oxo-3-phenyl-propyl)-imidazo[1,2-a]pyridine-6-carboxylic acid dimethylamide In a flame-dried flask filled with argon, the hydroxyketone 8-hydroxy-2,3-dimethyl-7-(3-oxo-3-phenyl-propyl)-imidazo[1,2-a]pyridine-6-carboxylic acid dimethylamide (3.00 g, 8.2 mmol) was suspended in dry DMF (30 ml). The mixture was treated with imidazole (0.95 g, 14.0 mmol) and was stiffed for several minutes until a clear solution was formed. Upon addition of thexyldimethylsilyl chloride (2.70 ml, 2.45 g, 13.7 mmol) a yellow solution was obtained, which was stirred for 1 hour at room temperature. The reaction mixture was poured onto a stirred mixture of ice (20 g), saturated ammonium chloride solution (20 ml), and dichloromethane (40 ml). Stirring was continued for several minutes, the phases were separated, and the aqueous phase was extracted with dichloromethane (2×15 ml). The combined organic phases were washed with water (20 ml), dried over sodium sulfate, and concentrated under reduced pressure. The residue, 5 g of a sticky, brown oil, was purified by flash chromatography [80 g of silica gel, eluant: petrol ether/ethyl acetate=8:2 (v/v)]. A sticky, colourless oil was isolated which was co-evaporated twice in the presence of dry toluene. After drying in vacuo, a colourless foamy solid (3.9 g, 94% yield) was obtained which was characterized by $^1$H-NMR spectroscopy as a mixture of the title compound (94 weight-%) and toluene (6 weight-%).

$^1$H-NMR (200 MHz, dmso-$d_6$): δ=0.38 (s, 6H), 0.83 (d, 6H), 0.89 (s, 6H), 1.74 (septet, 1H), 2.30 (s, 3 H+toluene), 236 (s, 3H), 2.90 (bs, 5H), 3.01 (s, 3H), 3.21 ($m_c$, 2H), 7.23 ($m_c$, toluene), 7.58 ($m_c$, 3H), 7.85 (s, 1H), 7.94 ($m_c$, 2H).

Conditions for the determination of purity by HPLC: Column: XTerra RP 18 150×4.6 mm 5 μm.—Eluant 0.01 M ($NH_4$)$HCO_3$ buffer (pH 8)/$CH_3CN$.—Gradient 90:10 (0 min) to 50:50 (15 min) to 20:80 (20 min), then isocratic.—Flow. 1 ml/min.—Temperature: 30° C.—Diode array detection at 240 nm.—Retention time: 23.47 min/99.20 area-%.

Use of Compounds of the Formula 1 for the Synthesis of Tricyclic Imidazopyridines of the Formula 5

I. 8-Hydroxy-7-[3R)-hydroxy-3-phenyl-propyl]-2,3-dimethyl-imidazo[1,2-a]pyridine-6-carboxylic acid dimethylamide In a flame dried flask filled with argon, the benzyl ether 8-benzyloxy-7-[(3R)-3-hydroxy-3-phenyl-propyl]-2,3-dimethyl-imidazo[1,2-a]pyridine-6-carboxylic acid dimethylamide (2.10 g, 4.6 mmol, sample contained 11 mol-% of the (3S)-enantiomer) was dissolved in ethanol (30 ml). The hydrogenation catalyst (10% Pd on charcoal, 020 g) and 1,4-cydohexadiene (2.2 ml, 1.9 g, 23 mmol) was added and the resulting black suspension was heated to 80° C. The reaction mixture was kept for 2 hours at this temperature and was then cooled to 0° C. The hydrogenation catalyst was removed by filtration and the filtrate was concentrated under reduced pressure. The crude product, 2 g of a dark-blue, foamy solid was purified by flash chromatography [50 g of silica gel, eluant dichloromethane/methanol=100:3 (v/v)]. The title compound (1.4 g, 83% yield) was obtained as a grey amorphous solid (melting point 180-182° C.), which was pure by means of $^1$H-NMR spectroscopy. The optical purity was confirmed by capillary electrophoresis (78.6% ee).

$^1$H-NMR (dmso-$d_6$, 200 MHz): δ=1.81 ($m_c$, 2H), 2.30, 2.33 (2 s, 6H), 2.50 ($bm_c$), 2.78, 2.91 (2 s, 6H), 4.49 (t, 1H), 7.25 (m, 5H), 7.59 (s, 1H).

Conditions for the separation of the enantiomers by capillary electrophoresis (Agilent CE-3D): Capillary: 64.5 cm×50 μm, bubble-cell (Agilent G 1600-61232).—Buffer: 50 mM sodium phosphate, pH 2.5 (Agilent 5062-8571).—Chiral selector: 40 mM trimethyl-β-cyclodextrin (Cyclolab) .—Voltage: 30 kV.—Temperature: 10° C.—Retention time (3S)-enantiomer: 20.05 min/10.7 area-%.—Retention time (3R)-enantiomer: 20.37 min/89.3 area-%.

II. 8-Hydroxy-7-[(3R)-3-hydroxy-3-phenyl-propyl]-2,3-dimethyl-imidazo[1,2-a]pyridine-6-carboxylic acid dimethylamide In a flame-dried flask filled with argon, the silyl ether 8-[dimethyl-1,1,2-trimethyl-propyl)-silanyloxy]-7-[(3R)-3-hydroxy-3-phenyl-propyl]-2,3-dimethyl-imidazo[1,2-a]pyridine-6-carboxylic acid dimethylamide (2.10 g, 4.1 mmol, sample contained 6 mol-% of the (3S)-enantiomer) was dissolved in dry THF (30 ml). At room temperature, a solution of tetrabutylammonium fluoride in THF (1 M, 420 ml, 4.2 mmol) was added slowly. A brown solution was obtained, which was stirred for 5 hours at room temperature. The reaction mixture was poured onto a mixture of saturated ammonium chloride solution (30 ml) and dichloromethane (50 ml). The phases were separated and the aqueous phase was extracted with dichloromethane (3×15 ml). The combined organic phases were washed with water (20 ml), dried over sodium sulfate, and concentrated under reduced pressure. A grey solid (2.6 g) remained which was treated with a mixture of acetone (1 ml) and diethyl ether (10 ml). The suspension was filtered, the residue was washed with diethyl ether and dried in vacuo. This afforded 1.6 g of the title compound still containing traces of impurities. After crystallization from ethyl acetate (100 ml) and isopropanol (10 ml), the spectroscopically pure title compound (1.3 g, 86% yield) was obtained as a grey crystalline solid. The optical purity was confirmed by capillary electrophoresis (85.2% ee).

$^1$H-NMR (dmso-$d_6$, 200 MHz): δ=1.81 ($m_c$, 2H), 2.30, 2.33 (2 s, 6H), 2.50 (bm$_c$), 2.78, 2.91 (2 s, 6H), 4.49 (t, 1H), 7.25 ($m_c$, 5H), 7.59 (s, 1H).

Conditions for the separation of the enantiomers by capillary electrophoresis (Agilent CE-3D): Capillary: 64.5 cm×50 μm, bubble-cell (Agilent G 1600-61232).—Buffer 50 mM sodium phosphate, pH 2.5 (Agilent 5062-571).—Chiral selector 40 mM trimethyl-β-cyclodextrin (Cyclolab). —Voltage: 30 kV.—Temperature: 10° C.—Retention time (3S)-enantiomer: 19.14 min/7.4 area-%.—Retention time (3R)-enantiomer: 19.4 min/92.6 area-%.

III. (9S)-2,3-Dimethyl-9-phenyl-7H-8,9-dihydro-pyrano[2,3-c]imidazo[1,2-]pyridine-6-carboxylic acid dimethylamide In a flame-dried flask filled with argon, 8-hydroxy-7-[(3R)-3-hydroxy-3-phenyl-propyl]-2,3-dimethyl-imidazo[1, 2-a]pyridine-6-carboxylic acid dimethylamide (78.6% ee, obtained by cleavage of the benzyloxy protecting group as described in experiment I., 180 mg, 0.49 mmol) was suspended in dry dichloromethane (5 ml) and triphenylphosphine (192 mg, 0.73 mmol) was added. After slow addition of diisopropyl azodicarboxylate (152 mg, 0.75 mmol) complete transformation of the starting material had occurred and a yellow-green solution was obtained. The reaction mixture was concentrated in vacuo and the crude product was purified by flash chromatography [20 g of silica gel, eluant dichloromethane/methanol=100:2 (v/v), yield: 170 mg] and subsequent treatment with acetone (2 ml). A colourless solid was obtained which was removed by filtration, washed with a mixture of acetone and diethyl ether [1:3 (v/v)], and dried in vacuo. The pure title compound (63 mg, 37% yield) showed a melting point of 248-250° C. The enantiomeric excess present in the starting material was conserved in the course of the Mitsunobu etherification as confirmed by HPLC analysis (78.3% ee) and by capillary electrophoresis (77.8% ee) of the tite compound.

$^1$H-NMR (200 MHz, dmso-$d_6$): δ=2.14 ($m_c$, 2H), 2.26, 2.35 (2 s, 6H), 2.42 ($m_c$), 2.75 ($m_c$, 1H), 2.87, 301 (2 s, 6H), 527 (dd, 1H), 7.43 (m, 5H), 7.79 (s, 1H).

Conditions for the determination of purity by HPLC: Column: CHIRAL-PAK® AD-H 250×4.6 mm, 5 μm.—Eluant ethanol/methanol=1:1 (v/v) with 0.1% of diethylamine.—Flow rate: 1 ml/min.—Temperature: 35° C.—Diode array detection at 243 nm.—Retention time: (9R)-enantiomer: 4.00 min/10.85 area-%; (9S)-enantiomer: 4.41 min/89.11 area-%.

Conditions for the separation of the enantiomers by capillary electrophoresis (Agilent CE-3D): Capillary. 64.5 cm×50 μm, bubble-cell (Agilent G 1600-61232).—Buffer 50 mM sodium phosphate, pH 2.5 (Agilent 5062871).—Chiral selector. 40 mM trimethyl-β-cyclodextrin (Cyclolab) .—Voltage: 30 kV.—Temperature: 10° C.—Retention time (9S)-enantiomer: 19.39 min /88.9 area-%.—Retention time (9R)-enantiomer: 20.12 min/11.1 area-%.

IV. (9S)-2,3-Dimethyl-9-phenyl-7H-8,9-dihydro-pyrano[2,3-c]imidazo[1,2-a]pyridine-6-carboxylic acid dimethylamide In a flame-dried flask filled with argon, 8-hydroxy-7-[(3R)-3-hydroxy-3phenyl-propyl]-2,3-dimethyl-imidazo[1,2-a]pyridine-6-carboxylic add dimethylamide (85.2% ee, obtained by cleavage of the dimethyl-(1,1,2-trimethyl-propyl)-silanyloxy protecting group as described in experiment II., 180 mg, 0.49 mmol) was suspended in dry dichloromethane (5 ml) and triphenylphosphine (192 mg, 0.73 mmol) was added. After slow addition of diisopropyl azodicarboxylate (152 mg, 0.75 mmol) complete transformation of the starting material had occurred and a yellow solution was obtained. The reaction mixture was concentrated in vacuo and the crude product was purified by flash chromatography [20 g of silica gel, eluant dichloromethane/methanol=100:2 (v/v), yield: 320 mg] and subsequent treatment with a mixture of acetone (1 ml) and diethyl ether (3 ml). A colourless solid was obtained which was removed by filtration, washed with little acetone and diethyl ether (3 ml), and dried in vacuo. The pure title compound (85 mg, 50% yield) showed a melting point of 252-254° C. The enantiomeric excess present in the starting material was conserved in the course of the Mitsunobu etherification as confirmed by HPLC analysis (86.0% ee) and by capillary electrophoresis (86.6% ee) of the title compound.

$^1$H-NMR (200 MHz, dmso-$d_6$): δ=2.14 ($m_c$, 2H), 2.26, 2.35 (2s, 6H), 2.42 ($m_c$), 2.75 ($m_c$, 1H), 2.87, 3.01 (2 s, 6H), 5.27 (dd, 1H), 7.43 ($m_c$, 5H), 7.79 (s, 1H).

Conditions for the determination of purity by HPLC: Column: CHIRALPAK® AD-H 250×4.6 mm, 5 μm.—Eluant ethanolmethanol=1:1 (v/v) with 0.1% of diethylamine.—Flow rate: 1 ml/min.—Temperature: 35° C.—Diode array detection at 243 nm.—Retention time: (9R)-enantiomer: 4.00 min/6.82 area-%; (9S)-enantiomer: 4.41 min/90.73 area-%.

Conditions for the separation of the enantiomers by capillary electrophoresis (Agilent CE-3D): Capillary. 64.5 cm×50 μm, bubble-ell (Agilent G 160041232).—Buffer 50 mM sodium phosphate, pH 2.5 (Agilent 50625571).—Chiral selector: 40 mM trimethyl-cyclodextrin (Cyclolab).—Voltage: 30 kV.—Temperature: 10° C.—Retention time (9S)-enantiomer: 19.65 min/93.3 area-%.—Retention time (3R)-enantiomer: 20.43 min/6.7 area-%.

Commercial Utility

The compounds of the formula 1 and their salts are valuable intermediates for the preparation of enantiomerically pure 7H-8,9-Dihydro-pyrano[2,3-c]imidazo-[1,2-a]pyridines of the formula 5. The compounds possess valuable pharmaceutical properties that make them commercially utilizable. In particular, they exhibit a marked inhibition of gastric acid secretion and an excellent gastric and intestinal protective action in warm-blooded animals, in particular humans.

We claim:
1. A compound of the formula 1

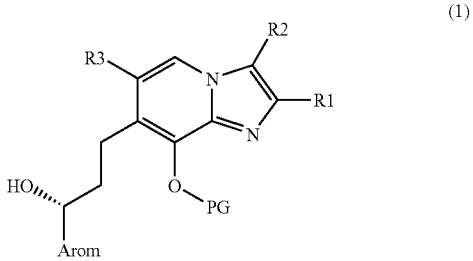

R1 is hydrogen, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl or hydroxy-1-4C-alkyl, R2 is hydrogen, 1-4C-alkyl, 3-7C-cycloalkyl, 3-7C-cycloalkyl-1-4C-alkyl, 1-4C-alkoxycarbonyl, hydroxy-1-4C-alkyl, hydroxy-3-4-C-alkenyl, hydroxy-3-4C-alkinyl, halogen, 2-4C-alkenyl, 2-4C-alkynyl, fluoro-1-4C-alkyl, cyanomethyl, 1-4C-alkoxy, 1-4C-alkylcarbonylamino, 1-4C-alkoxycarbonylamino, 1-4C-alkoxy-1-4C-alkoxycarbonylamino, 1-4C-alkylcarbonyl, 2-4C-alkenylcarbonyl, 2-4C-alkinylcarbonyl or the radical —CO—NR21R22,
where
R21 is hydrogen, 1-7C-alkyl, hydroxy-1-4C-alkyl, 1-4C-alkoxy-1-4C-alkyl or 3-7C-cycloalkyl and
R22 is hydrogen, 1-7C-alkyl, hydroxy-1-4C-alkyl, 1-4C-alkoxy-1-4C-alkyl or 3-7C-cycloalkyl,
or where
R21 and R22 together and including the nitrogen atom to which they are attached form a pyrrolidino, piperidino, morpholino, aziridino or azetidino radical, R3 is hydroxy-1-4C-alkyl, 1-4C-alkoxy-1-4C-alkyl, 1-4C-alkoxy-1-4C-alkoxy-1-4C-alkyl, 1-4C-alkoxycarbonyl, fluoro-1-4C-alkoxy-1-4C-alkyl, a imidazolyl, tetrazolyl or oxazolyl radical or the radical —CO—NR31R32,
where
R31 is hydrogen, 1-7C-alkyl, hydroxy-1-4C-alkyl, 1-4C-alkoxy-1-4C-alkyl or 3-7C-cycloalkyl and
R32 is hydrogen, 1-7C-alkyl, hydroxy-1-4C-alkyl, 1-4C-alkoxy-1-4C-alkyl or 3-7C-cycloalkyl,
or where
R31 and R32 together and including the nitrogen atom to which they are attached form a pyrrolidino, piperidino, morpholino, aziridino or azetidino radical, Arom is a R4-, R5-, R6- and R7-substituted mono- or bicyclic aromatic radical selected from the group consisting of phenyl, naphthyl, pyrrolyl, pyrazolyl, imidazolyl, 1,2,3triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl,
where
R4 is hydrogen, 1-4C-alkyl, hydroxy-1-4C-alkyl, 1-4C-alkoxy, 2-4C-alkenyloxy, 1-4C-alkylcarbonyl, 1-4C-alkoxycarbonyl, carboxy-1-4C-alkyl, 1-4C- alkoxycarbonyl-1-4C-alkyl, halogen, aryl, aryl-1-4C-alkyl, aryloxy, aryl-1-4C-alkoxy, trifluoromethyl, nitro, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen or trifluoromethyl, R6 is hydrogen, 1-4C-alkyl or halogen and R7 is hydrogen, 1-4C-alkyl or halogen, PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical SO$_2$—R11, wherein R8, R9, R10 are independently from each other 1-7C-alkyl, aryl or aryl-1-4C-alkyl, R11 is 1-4C-alkyl or aryl, where aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy and cyano, or a salt thereof.

2. A compound of the formula 1 as claimed in claim 1, in which

R1 is hydrogen, 1-4C-alkyl, 3-7C-cycloalkyl, 1-4C-alkoxy-1-4C-alkyl or 1-4C-alkoxycarbonyl, R2 is hydrogen, 1-4C-alkyl, halogen, 2-4C-alkenyl, 2-4C-alkynyl, hydroxy-1-4C-alkyl, 3-7C-cycloalkyl, 1-4C-alkoxycarbonyl or the radical—CO—NR21R22, where R21 is hydrogen, 1-4C-alkyl or 1-4C-alkoxy-1-4C-alkyl, R22 is hydrogen, 1-4C-alkyl or 1-4C-alkoxy-1-4C-alkyl, R3 is hydroxyl-1-4C-alkyl, 1-4C-alkoxy-1-4C-alkyl, 1-4C-alkoxy-1-4C-alkoxy-1-4C-alkyl, 1-4-C-alkoxycarbonyl or the radical—CO—NR31R32, where R31 is hydrogen, 1-7C-alkyl, hydroxy-1-4C-alkyl, 1-4C-alkoxy-1-4C-alkyl or 3-7C-cycloalkyl and R32 is hydrogen, 1-7C-alkyl, hydroxy-1-4C-alkyl, 1-4C-alkoxy-l4C-alkyl or 3-7C-cycloalkyl, or where R31 and R32 together and including the nitrogen atom to which they are attached are a pyrrolidino, piperidino, morpholino, aziridino or azetidino radical, Arom is a R4-, R5-, R6- and R7-substituted mono- or bicyclic aromatic radical selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where R4 is hydrogen, 1-4C-alkyl, hydroxy-1-4C-alkyl, 1-4C-alkoxy, 2-4C-alkenyloxy, 1-4C-alkoxycarbonyl, carboxy-1-4C-alkyl, 1-4C-alkoxycarbonyl-1-4C--alkyl, halogen, aryl, aryl1-4C-alkyl, aryloxy, aryl1-4C-alkoxy, trifluoromethyl, nitro, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen or trifluoromethyl, R6 is hydrogen, 1-4C-alkyl or halogen and R7 is hydrogen, 1-4C-alkyl or halogen, PG is 1-4C-alkyl, 1-4C-alkoxy1-4C-alkyl, aryl1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical SO$_2$—R11, wherein R8, R9, R10 are independently from each other 1-7C-alkyl, aryl or aryl-1-4C-alkyl, R11 is 1-4C-alkyl or aryl, where aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy and cyano, or a salt thereof.

3. A compound of the formula 1 as claimed in claim 1, in which

R1 is 1-4C-alkyl or 3-7C-cycloalkyl,

R2 is 1-4C-alkyl, halogen, hydroxy-1-4C-alkyl, 2-4C-alkenyl, 2-4C-alkynyl, 3-7C-cycloalkyl, or the radical—CO—NR21R22, where R21 is hydrogen or 1-4C-alkoxy-1-4C-alkyl, R22 is hydrogen or 1-4C-alkoxy-1-4C-alkyl, R3 is hydroxy-1-4C-alkyl, 1-4C-alkoxy-1-4C-alkyl, 1-4C-alkoxy-1-4C-alkoxy-1-4C-alkyl, or the radical—CO—NR31R32, where R31 is hydrogen, 1-7C-alkyl, hydroxy-1-4C-alkyl, 1-4C-alkoxy-1-4C-alkyl or 3-7C-cycloalkyl and R32 is hydrogen, 1-7C-alkyl, hydroxy-1-4C-alkyl, 1-4C-alkoxy-1-4C-alkyl or 3-7C-cycloalkyl, or where R31 and R32 together and including the nitrogen atom to which they are attached are a pyrrolidino, piperidino, morpholino, aziridino or azetidino radical, Arom is a R4-, R5-, R6- and R7-substituted mono- or bicyclic aromatic radical selected from the group consisting of phenyl, naphthyl, pyrrolyl, pyrazolyl, imidazolyl, 1,2,3triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where R4 is hydrogen, 1-4C-alkyl, hydroxy-1-4C-alkyl, 1-4C-alkoxy, 2-4C-alkenyloxy, 1-4C-alkoxycarbonyl, carboxy-1-4C-alkyl, 1-4C-alkoxycarbonyl-1-4C-alkyl, halogen, aryl, aryl-1-4C-alkyl, aryloxy, aryl-1-4C-alkoxy, trifluoromethyl, nitro, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen or trifluoromethyl, R6 is hydrogen, 1-4C-alkyl or halogen and R7 is hydrogen, 1-4C-alkyl or halogen, PG is 1-4C-alkyl, l4C-alkoxy-1-4C-alkyl, aryl-1-4C-alkoxy-14C-alkyl, 14C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkyl-carbonyl, aryl-1-4C-alkoxycarbonyl, a radical SiR8R9R10 or a radical $SO_2$—R11, wherein R8, R9, R10 are independently from each other 1-7C-alkyl, aryl or aryl-1-4C-alkyl, R11 is 1-4C-alkyl or aryl where aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy and cyano, or a salt thereof.

4. A compound of the formula 1 as claimed in claim 1, in which

R1 is 1-4C-alkyl,

R2 is 1-4C-alkyl, halogen, hydroxy-1-4C-alkyl, 2-4C-alkenyl, 2-4C-alkynyl, 3-7C-cycloalkyl, or the radical—CO—NR21R22, where R21 is hydrogen or 1-4C-alkoxy-1-4C-alkyl, R22 is hydrogen or 1-4C-alkoxy-1-4C-alkyl, R3 is hydroxy1-4C-alkyl, 1-4C-alkoxy-1-4C-alkyl, 1-4C-alkoxy1-4C-alkoxy-1-4C-alkyl, or the radical—CO—NR31R32, where R31 is hydrogen, 1-7C-alkyl or 3-7C-cycloalkyl, R32 is hydrogen, 1-7C-alkyl or 3-7C-cycloalkyl, or where R31 and R32 together and including the nitrogen atom to which they are attached are a pyrrolidino, piperidino, morpholino, aziridino or azetidino radical, Arom is a R4- and R5-substituted phenyl, pyrrolyl, furanyl (furyl), thiophenyl (thienyl) or pyridinyl, where R4 is hydrogen, 1-4C-alkyl, hydroxy-1-4C-alkyl, 1-4C-alkoxy or halogen, R5 is hydrogen, 1-4C-alkyl, 1-4C-alkoxy or halogen, PG is 1-4C-alkyl, 1-4C-alkoxy-1-4C-alkyl, aryl1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkyl-carbonyl, aryl-1-4C-alkoxycarbonyl, a radical SiR8R9R10 or a radical $SO_2$—R11, wherein R8, R9, R10 are independently from each other 1-7C-alkyl, aryl or aryl-1-4C-alkyl, R11 is 1-4C-alkyl or aryl, where aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy and cyano, or a salt thereof.

5. A compound of the formula 1 as claimed in claim 1, in which

R1 is 1-4C-alkyl,

R2 is 1-4C-alkyl, halogen, hydroxy-1-4C-alkyl, 2-4C-alkenyl, 2-4C-alkynyl, 3-7C-cycloalkyl, or the radical—CO—NR21R22, where R21 is hydrogen or 1-4C-alkoxy-1-4C-alkyl, R22 is hydrogen or 1-4C-alkoxy-1-4C-alkyl, R3 is the radical—CO—NR31R32, where R31 is hydrogen, 1-7C-alkyl or 3-7C-cycloalkyl, R32 is hydrogen, 1-7C-alkyl or 3-7C-cycloalkyl, or where R31 and R32 together and including the nitrogen atom to which they are attached are a pyrrolidino, piperidino, morpholino, aziridino or azetidino radical, Arom is a R4- and R5-substituted phenyl, where R4 is hydrogen, 1-4C-alkyl, hydroxy-1-4C-alkyl, 1-4C-alkoxy or halogen, R5 is hydrogen, 1-4C-alkyl or halogen, PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkyl-carbonyl, aryl-1-4C-alkoxycarbonyl, a radical SiR8R9R10 or a radical $SO_2$—R11, wherein R8, R9, R10 are independently from each other 1-7C-alkyl, aryl or aryl-1-4C-alkyl, R11 is 1-4C-alkyl or aryl, where aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy and cyano, or a salt thereof.

6. A compound of the formula 1 as claimed in claim 1, in which

R1 is 1-4C-alkyl,

R2 is 1-4C-alkyl, halogen, hydroxy-1-4C-alkyl, 2-4C-alkenyl, 2-4C-alkynyl, 3-7C-cycloalkyl or the radical—CO—NR21R22, where R21 is hydrogen or 1-4C-alkoxy-1-4C-alkyl, R22 is hydrogen or 1-4C-alkoxy-1-4C-alkyl, R3 is the radical—CO—NR31R32, where R31 is hydrogen, 1-7C-alkyl or 3-7C-cycloalkyl, R32 is hydrogen, 1-7C-alkyl or 3-7C-cycloalkyl, or where R31 and R32 together and including the nitrogen atom to which they are attached are a pyrrolidino, piperidino, morpholino, aziridino or azetidino radical, Arom is phenyl, PG is 1-4C-alkyl, 1-4C-alkoxy-1-4C-alkyl, aryl1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkyl-carbonyl, aryl-1-4C-alkoxycarbonyl, a radical SiR8R9R10 or a radical $SO_2$—R11, wherein R8, R9, R10 are independently from each other 1-7C-alkyl, aryl or aryl1-4C-alkyl, R11 is 1-4C-alkyl or aryl, where
aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy and cyano, or a salt thereof.

7. A compound of the formula 1 as claimed in claim 1, in which
R1 is 1-4C-alkyl,
R2 is 1-4C-alkyl, halogen or hydroxy-1-4C-alkyl,
R3 is the radical—CO—NR31R32,
where
R31 is hydrogen, 1-7C-alkyl or 3-7C-cycloalkyl,
R32 is hydrogen, 1-7C-alkyl or 3-7C-cycloalkyl,
or where
R31 and R32 together and including the nitrogen atom to which they are attached are a pyrrolidino radical,
Arom is phenyl,
PG is 1-4C-alkyl, 1-4C-alkoxy-1-4C-alkyl, aryl-1-4C-alkoxy-1-4C-alkyl, 1-4C-alkoxy-1-4C-alkoxy-1-4C-alkyl, 1-4C-alkoxy-1-4C-alkyl substituted by a SiR8R9R10 radical, tetrahydropyran, tetrahydrofuran, aryl-1-4C-alkyl, 3-7C-cycloalkyl, 1-4C-alkylcarbonyl, aryl-carbonyl, 1-4C-alkoxycarbonyl, aryl-1-4C-alkylcarbonyl, aryl-1-4C-alkoxycarbonyl, a radical SiR8R9R10 or a radical SO$_2$—R11,
wherein
R8, R9, R10 are independently from each other 1-7C-alkyl, aryl or aryl1-4C-alkyl,
R11 is 1-4C-alkyl or aryl,
where
aryl is phenyl or substituted phenyl having one, two or three identical or different substituents selected from the group consisting of 1-4C-alkyl, 1-4C-alkoxy, carboxyl, 1-4C-alkoxycarbonyl, halogen, trifluoromethyl, nitro, trifluoromethoxy and cyano, or a salt thereof.

8. A compound of the formula 1 as claimed in claim 1, in which
R1 is 1-4C-alkyl,
R2 is 1-4C-alkyl,
R3 is the radical—CO—NR31R32,
where
R31 is 1-4C-alkyl,
R32 is 1-4C-alkyl,
Arom is phenyl,
PG is aryl1-4C-alkyl or a radical SiR8R9R10
wherein
R8 is 1-7C-alkyl,
R9 is 1-7C-alkyl,
R10 is 1-7C-alkyl,
where
aryl is phenyl, or a salt thereof.

9. A process for the preparation of a compound of the formula 1 as claimed in claim 1, in which R1, R2, R3, Arom and PG have the meanings as indicated in claim 1, which comprises asymmetrically reducing a compound of the formula 3,

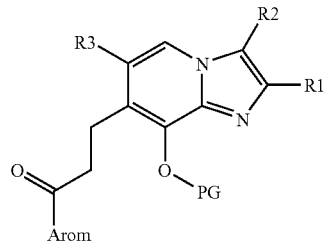

(3)

in which R1, R2, R3, Arom and PG have the meanings as indicated in claim 1.

10. The process as claimed in claim 9, which comprises submitting a compound of the formula 3, to a asymmetric catalytic hydrogenation reaction.

11. A process of preparing a compound of the formula 4 or a salt thereof,

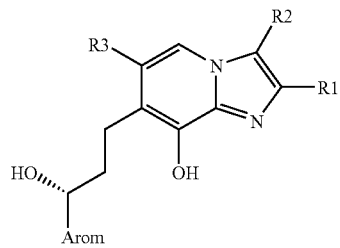

(4)

in which R1, R2, R3 and Arom have the meanings as indicated in claim 1, comprising deprotection of a compound of formula 1 as claimed in claim 1.

12. A process of preparing a compound of the formula 5 or a salt thereof,

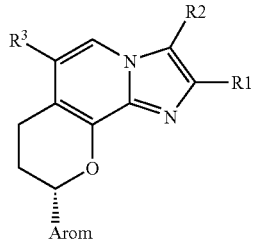

(5)

in which R1, R2, R3 and Arom have the meanings as indicated in claim 1, comprising deprotection of a compound of formula 1 as claimed in claim 1 and obtaining a compound of the formula 4

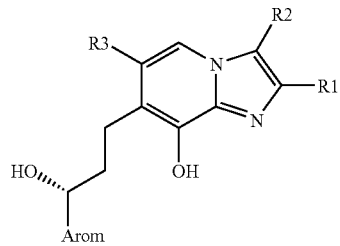

(4)

and submitting said compound of formula 4 to a cyclization reaction.

* * * * *

UNITED STATES PATENT AND TRADEMARK OFFICE
CERTIFICATE OF CORRECTION

PATENT NO. : 7,326,784 B2
APPLICATION NO. : 10/582609
DATED : February 5, 2008
INVENTOR(S) : Palmer et al.

It is certified that error appears in the above-identified patent and that said Letters Patent is hereby corrected as shown below:

Claim 1, Column 28, Line 59,
Please delete "1,2,3triazolyl"
and
replace with
-- 1,2,3-triazolyl --

Claim 2, Column 29, Line 48,
Please delete "1-4C-alkoxy-14C-alkyl"
and
replace with
-- 1-4C-alkoxy-1-4C-alkyl --

Claim 2, Column 29, Line 66,
Please delete "aryl1-4C-alkoxy"
and
replace with
-- aryl-1-4C-alkoxy --

Claim 2, Column 30, Lines 7-8,
Please delete "aryl1-4C-alkoxy-1-4C-alkyl"
and
replace with
-- aryl-1-4C-alkoxy-1-4C-alkyl --

Claim 3, Column 30, Line 50,
Please delete "1,2,3triazolyl"
and
replace with
-- 1,2,3-triazolyl --

Claim 3, Column 31, Line 1,
Please delete "14C-alkoxy-1-4C-alkyl"
and
replace with
-- 1-4C-alkoxy-1-4C-alkyl --

UNITED STATES PATENT AND TRADEMARK OFFICE
CERTIFICATE OF CORRECTION

PATENT NO. : 7,326,784 B2
APPLICATION NO. : 10/582609
DATED : February 5, 2008
INVENTOR(S) : Palmer et al.

It is certified that error appears in the above-identified patent and that said Letters Patent is hereby corrected as shown below:

Claim 3, Column 31, Lines 1-2,
Please delete "aryl-1-4C-alkoxy-14C-alkyl"
and
replace with
-- aryl-1-4C-alkoxy-1-4C-alkyl --

Claim 3, Column 31, Lines 2-3,
Please delete "14C-alkoxy-1-4C-alkoxy-1-4C-alkyl"
and
replace with
-- 1-4C-alkoxy-1-4C-alkoxy-1-4C-alkyl --

Claim 4, Column 31, Line 28,
Please delete "hydroxyl-4C-alkyl"
and
replace with
-- hydroxy-1-4C-alkyl --

Claim 4, Column 31, Lines 28-29,
Please delete "1-4C-alkoxy1-4C-alkoxy-1-4C-alkyl"
and
replace with
-- 1-4C-alkoxy-1-4C-alkoxy-1-4C-alkyl --

Claim 4, Column 31, Lines 43-44,
Please delete "aryl1-4C-alkoxy-1-4C-alkyl"
and
replace with
-- aryl-1-4C-alkoxy-1-4C-alkyl --

Claim 6, Column 32, Lines 56-57,
Please delete "aryl1-4C-alkoxy-1-4C-alkyl"
and
replace with
-- aryl-1-4C-alkoxy-1-4C-alkyl --

UNITED STATES PATENT AND TRADEMARK OFFICE
CERTIFICATE OF CORRECTION

PATENT NO. : 7,326,784 B2
APPLICATION NO. : 10/582609
DATED : February 5, 2008
INVENTOR(S) : Palmer et al.

It is certified that error appears in the above-identified patent and that said Letters Patent is hereby corrected as shown below:

Claim 6, Column 32, Line 66,
Please delete "aryll-4C-alkyl"
and
replace with
-- aryl-1-4C-alkyl --

Claim 7, Column 33, Line 43,
Please delete "aryll-4C-alkyl"
and
replace with
-- aryl-1-4C-alkyl --

Claim 8, Column 33, Line 54,
Please delete "aryll-4C-alkyl"
and
replace with
-- aryl-1-4C-alkyl --

Claim 9, Column 33, Line 64,
Please delete "formula las claimed in claim 1, in which"
and
replace with
-- formula 1, in which --

Signed and Sealed this

Eighth Day of July, 2008

JON W. DUDAS
*Director of the United States Patent and Trademark Office*